US006462248B1

(12) United States Patent
Nakatani et al.

(10) Patent No.: US 6,462,248 B1
(45) Date of Patent: Oct. 8, 2002

(54) METHOD FOR PRODUCING AROMATIC COMPOUNDS HAVING ALKYL GROUP WITH AT LEAST THREE CARBON ATOMS

(75) Inventors: Jiro Nakatani, Nagoya; Eiichi Minomiya, Okazaki; Masahiro Inohara; Kazuyoshi Iwayama, both of Nagoya; Tetsuya Kato, Kamakura, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/385,270

(22) Filed: Aug. 30, 1999

(30) Foreign Application Priority Data

Sep. 9, 1998 (JP) ............................................. 10-255098
Nov. 19, 1998 (JP) ............................................. 10-329944

(51) Int. Cl.[7] ............................ C07C 25/08; C07C 5/27
(52) U.S. Cl. ........................ 585/475; 585/469; 585/470; 585/471
(58) Field of Search ..................... 585/469, 470, 585/471, 475, 435, 452, 446, 453, 454, 477, 481

(56) References Cited

U.S. PATENT DOCUMENTS 3,268,607 A * 8/1966 Schmidt et al. ............. 260/668
3,855,333 A * 12/1974 Neuzil .................. 260/674 SA (List continued on next page.)

FOREIGN PATENT DOCUMENTS

EP   0 322 869     7/1989

(List continued on next page.)

OTHER PUBLICATIONS

"Mechanism of n–Propyltoluene Formation in $C_3$ Alkylation of Toluene: The Effect of Zeolite Structural Type," by Blanka Wichterlova and Jiri Cejka, *Journal of Catalysis*, 146, 523–529 (1994).
"Factors Controlling iso–/n–and para–selectivity in the alkylation of toluene with isopropanol on molecular sieves," by Jiri Cejka, Gennadij A. Kapustin and Blanka Wichterlova, *Applied Catalysis A: General*, 108 (1994) 187–204.

*Primary Examiner*—Bekir L. Yildirim
(74) *Attorney, Agent, or Firm*—Schnader Harrison Segal & Lewis LLP

(57) ABSTRACT

Aromatic compounds having an alkyl group with at least 3 carbon atoms are produced in a process comprising at least one of the following steps:

(1) a step of contacting a starting material that contains an aromatic compound having a branched alkyl group with at least 3 carbon atoms, with a zeolite-containing catalyst in a liquid phase in the presence of hydrogen therein, thereby changing the position of the carbon atoms of the alkyl group bonding to the aromatic ring of the compound;

(2) a step of contacting a starting material that contains an aromatic compound having a branched alkyl group with at least 3 carbon atoms, with a catalyst containing zeolite and containing rhenium and/or silver, in a liquid phase, thereby changing the position of the carbon atoms of, the alkyl group bonding to the aromatic ring of the compound;

(3) a step of contacting a halogenated aromatic compound having an alkyl group with at least 3 carbon atoms, with an acid-type catalyst, thereby isomerizing the compound;

(4) a step of treating a mixture of isomers of an aromatic compound having an alkyl group with at least 3 carbon atoms, with a zeolite adsorbent that contains at least one exchangable cation selected from alkali metals, alkaline earth metals, lead, thallium and silver, thereby separating a specific isomer from the isomer mixture through adsorption.

10 Claims, 4 Drawing Sheets

U.S. PATENT DOCUMENTS

| | | | | |
|---|---|---|---|---|
| 3,996,305 A | * | 12/1976 | Berger | 260/672 T |
| 3,996,306 A | * | 12/1976 | Korous et al. | 260/674 SA |
| 4,181,811 A | * | 1/1980 | Young | 585/486 |
| 4,230,894 A | * | 10/1980 | Young | 568/768 |
| 4,324,941 A | * | 4/1982 | Ghirga et al. | 485/466 |
| 4,393,262 A | * | 7/1983 | Kaeding | 585/467 |
| 4,580,000 A | | 4/1986 | Wu | |
| 4,806,698 A | * | 2/1989 | Rule et al. | 570/202 |
| 4,827,069 A | * | 5/1989 | Kushnerick et al. | 585/415 |
| 4,891,458 A | * | 1/1990 | Innes et al. | 585/323 |
| 5,202,516 A | | 4/1993 | Lee et al. | |
| 5,396,010 A | * | 3/1995 | Harandi et al. | 585/418 |
| 5,414,172 A | * | 5/1995 | Chin et al. | 585/322 |
| 5,641,393 A | * | 6/1997 | Nakagawa | 208/46 |
| 6,111,157 A | * | 8/2000 | Hendriksen | 585/467 |

FOREIGN PATENT DOCUMENTS

| | | |
|---|---|---|
| EP | 0 940 177 | 9/1999 |
| EP | 0 037 168 | 10/2001 |
| GB | 1 292 228 | 10/1992 |
| JP | 55 164631 | 12/1980 |
| JP | 59 141525 | 8/1984 |
| JP | 01 066131 | 3/1989 |
| JP | 01 319444 | 12/1989 |
| JP | 02 229122 | 9/1990 |
| JP | 08 104657 | 4/1996 |
| WO | WO 89/12613 | 12/1989 |
| WO | WO 98/24745 | 6/1998 |

* cited by examiner

METHOD FOR PRODUCING AROMATIC COMPOUNDS HAVING ALKYL GROUP WITH AT LEAST THREE CARBON ATOMS

BACKGROUND OF THE INVENTION

1. Field of the Invention

The present invention relates to a method for producing of aromatic compounds having an alkyl group with at least 3 carbon atoms, which are useful as starting materials for production of various pharmaceuticals and agricultural chemicals, through conversion, isomerization and/or adsorptive separation of aromatic compounds, and also to catalysts and adsorbents for the method.

2. Description of the Related Art

In aromatic compounds having a branched alkyl group with at least 3 carbon atoms, in general, it is difficult to change the positions of the carbon atoms of the alkyl group that is bonded to the aromatic ring. Especially, in those, compounds the steps of (A) reducing the number of the branches of the alkyl group, (B) shortening the branched side chains of the alkyl group and (C) changing the alkyl group into a different one that is bonded to the aromatic ring via a secondary carbon are difficult.

One example of changing the position of the carbon atoms of an alkyl group bonding to an aromatic ring, thereby reducing the number of the branches of the alkyl group is represented by the following chemical reaction formula:

(formula 2)

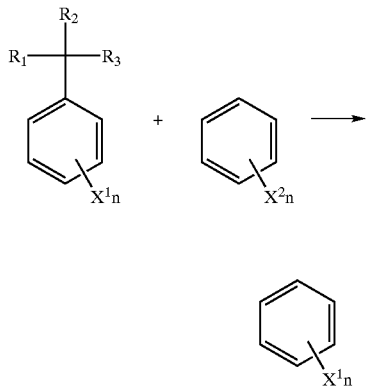

wherein
$R_1$ to $R_5$ each represents a methyl, an ethyl group, or a linear alkyl group with at least 3 carbon atoms;
$X^1$ and $X^2$ each represent a methyl group, an ethyl group, a halogen atom, a formyl group, a carboxyl group, an alkoxy group, a nitro group, an amino group, or a cyano group;
n is from 0 to 5.

Another example of changing the position of the carbon atoms of an alkyl group bonding to an aromatic ring, thereby shortening the branched side chains of the alkyl group is represented by the following chemical reaction formula:

(formula 3)

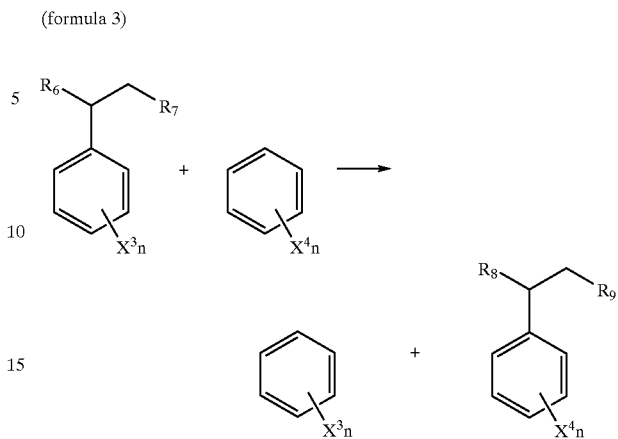

wherein
$R_6$ represents an ethyl group, or a linear alkyl group with at least 3 carbon atoms;
$R_8$ represents a hydrogen atom, or an alkyl group of which the carbon chain is shorter than that of R6;
$R_7$ and $R_9$ each represents an alkyl group;
X3 and X4 each represent a methyl group, an ethyl group, a halogen atom, a formyl group, a carboxyl group, an alkoxy group, a nitro group, an amino group, or a cyano group;
n is from 0 to 5.

Still another example of changing the position of the carbon atoms of an alkyl group bonding to an aromatic ring, thereby changing the alkyl group into a different one bonding to the aromatic ring via a secondary carbon is represented by the following chemical reaction formula:

(formula 4)

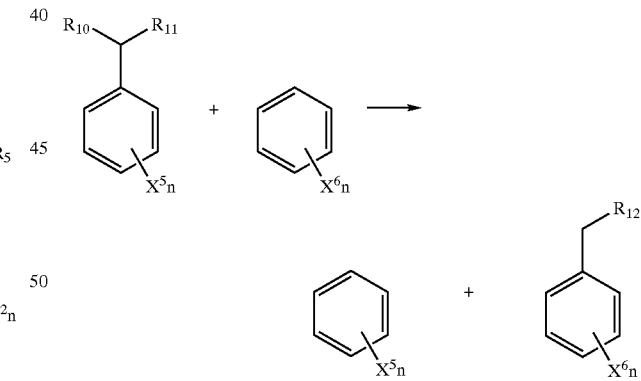

wherein
$R_{10}$ to $R_{12}$ each represents an alkyl group,
$X^5$ and $X^6$ each represent a methyl group, an ethyl group, a halogen atom, a formyl group, a carboxyl group, an alkoxy group, a nitro group, an amino group, or a cyano group;
n is from 0 to 5.

Concretely, alkylating benzene with propylene give a main product of isopropylbenzene in which the branched alkyl group directly bonds to the aromatic ring via its tertiary carbon, but gives a minor side product of n-propylbenzene in which the non-branched alkyl group directly bonds to the aromatic ring via its secondary carbon. In the main product of isopropylbenzene, the isopropyl group is stabilized. In this, therefore, it is difficult to change the configuration of the alkyl group bonding to the aromatic ring so as to change the isopropylbenzene into n-propylbenzene. The same shall apply to any other aromatic compounds having a higher alkyl group. Anyhow, it is known that alkyl group-substituted aromatic compounds, in which the number of the branches of the alkyl group is small and/or the branched side chains of the alkyl group are short and/or the alkyl group bonds to the aromatic group via a secondary carbon, are difficult to produce. Therefore, in order to obtain n-alkyl group-substituted aromatic compounds, generally employed is a method of alkylating aromatic compounds with an n-alkyl halide or an n-alkyl alcohol. However, the method is not always satisfactory in industrial use, since the reagents to be used are expensive and since the n-alkyl group-substituted aromatic compounds produced are partly isomerized. Another method is known, which comprises alkylating toluene with ethylene in the presence of an alkali catalyst, but this is still unsatisfactory in industrial use. Given that situation, it is desired to develop efficient and inexpensive methods for producing n-alkyl group-substituted aromatic compounds.

Japanese Patent Laid-Open No. 141525/1984 discloses an inexpensive method of producing benzene compounds having an n-alkyl group from inexpensive starting materials. In the method, an alkylbenzene having a branched alkyl group, of which the number of carbon atoms is the same as that of carbon atoms of the n-alkyl group in the intended product, is contacted with zeolite catalyst along with a benzene derivative. *Journal of Catalysis*, Vol. 146, pp. 523–529, 1994, and *Applied Catalysis A*, Vol. 108, pp. 187–204, 1994 disclose vapor-phase alkylation of toluene with isopropanol and propanol in the presence of a zeolite catalyst, in which the initial-stage product of methylisopropylbenzene is transalkylated with the starting toluene or benzene into n-alkylbenzenes.

Halogenated aromatic compounds having an alkyl group with at least 3 carbon atoms are produced from aromatic compounds having an alkyl group with at least 3 carbon atoms through nucleophilic substitution with halogens such as chlorine and bromine. The halogenation is extremely specific to ortho (o-) and para (p-) orientation. Therefore, for obtaining meta (m-) isomer through the reaction, the product must be isomerized. The ratio of isomers of halogenated aromatic compounds having an alkyl group with at least 3 carbon atoms that are demanded in the market often differs from that of those isomers that are actually produced through halogenation. Therefore, for effectively utilizing halogenated aromatic compounds having an alkyl group with at least 3 carbon atoms, the isomerization of the compounds has an important technical meaning. Specifically, the isomerization referred to herein is to change the relative position of the halogen and the alkyl group on the aromatic ring of halogenated aromatic compounds, and does not include isomerization of the alkyl group itself. As conventional examples of isomerization of aromatic compounds, generally known are a method of using a catalyst of aluminium trichloride or the like such as that disclosed in *J. Org. Chem.*, Vol. 27, p. 3464, 1962; and a method of using a catalyst of HF-BF3 such as that disclosed in Japanese Patent Laid-Open No. 11809/1971. Apart from those, *Acta Chemica Scandinavia*, Vol. B39, p. 437, 1985, and Japanese Patent Laid-Open No. 316600/1998 disclose isomerization of chloroethylbenzene with mordenite-type zeolite. Japanese Patent Laid-Open Nos. 40428/1982, 85330/1982, 163327/1982 and 309792/1995 disclose isomerization of halogenotoluenes with a catalyst of zeolite.

A compound having a higher alkyl group shall include isomers, depending on the number of the branches of the alkyl group therein, and the isomers generally have similar properties (boiling point, melting point, solubility). Therefore, it is often difficult to isolate the isomers through distillation or crystallization.

Di-substituted benzenes will be discussed. Dialkylbenzenes with alkyl groups having 1 or 2 carbon atoms have three types of isomers which are o-isomer, m-isomer and p-isomer. Of alkyl groups having 3 or more carbon atoms, however, one having 3 carbon atoms includes two types propyl groups which are n-propyl group and isopropyl group, and one having 4 carbon atoms includes four types of butyl groups which are n-butyl group, isobutyl group, sec-butyl group and tert-butyl group. Each of those alkyl group shall give three types of isomers, o-isomer, m-isomer and p-isomer, when existing in dialkylbenzenes. As a result, dialkylbenzenes with alkyl groups having 3 or more carbon atoms shall include such an extremely large number of isomers.

The boiling point difference between those aromatic compound isomers is extremely small, and a precision distillation tower having a large number of stages must be used for isolating the isomers. In that situation, it has heretofore been difficult to efficiently isolate an intended aromatic compound having an alkyl group with at least 3 carbon atoms, at high purity.

For separating chlorotoluene isomers, of which the structure differs from that of the aromatic compounds for the present invention, Japanese Patent Laid-Open No. 5155/1962 discloses an adsorptive separation method of using an X-type zeolite as the adsorbent, and Japanese Patent Laid-Open Nos. 31627/1982, 35528/1982 and 91933/1982 disclose an adsorptive separation method of using a K ion-exchanging Y-type zeolite as the adsorbent. In those methods, the adsorbents used have the ability to separate the m-isomer from the p-isomer through adsorption but do not have the ability to separate the m-isomer from the o-isomer through adsorption. In those, therefore, it is impossible to isolate m-chlorotoluene alone as the extract or raffinate component. Japanese Patent Laid-Open Nos. 131923/1983 and 176223/1984 disclose a method of separating m-chlorotoluene through adsorption, in which are used an Ag-K ion-exchanging Y-type zeolite and an Na-Cu ion-exchanging Y-type zeolite, respectively, as the adsorbent. In the method disclosed, m-chlorotoluene is isolated as the raffinate component.

In the methods noted above of processing aromatic compounds having a branched alkyl group with at least 3 carbon atoms for changing the position of the carbon atoms of the alkyl group bonding to the aromatic ring, the yield of the intended products is poor. In those, in addition, the amount of the alkyl group-substituted aromatic compounds to be recovered after the reaction is not satisfactory, or that is, the loss of the alkyl group-substituted aromatic compounds is great. Still another problem with those methods is that the activity of the catalyst used is lowered with the lapse of the reaction time. For these reasons, the methods are unfavorable to industrial use for changing the position of the carbon atoms of alkyl groups bonding to aromatic rings.

Being different from the methyl group and the ethyl group in halogenotoluenes and halogenoethylbenzenes, the alkyl group having at least 3 carbon atoms in alkyl-substituted halogenoaromatic compounds is readily dealkylated from the aromatic ring, and efficient isomerization of those halogenoaromatic compounds is difficult.

No adsorptive separation method has heretofore been known for separating specific isomers from a mixture of aromatic compounds having an alkyl group with at least 3 carbon atoms.

SUMMARY OF THE INVENTION

The object of the present invention is to provide an industrializable and highly productive method for producing aromatic compounds having an alkyl group with at least 3 carbon atoms, which comprises at least one of the following: a step of changing the position of the carbon atoms of the alkyl group bonding to the aromatic ring of an aromatic compound having an alkyl group with at least 3 carbon atoms, a step of isomerizing a halogenated aromatic compound having an alkyl group with at least 3 carbon atoms, and a step of separating an aromatic compound having an alkyl group with at least 3 carbon atoms through adsorption.

We, the present inventors have assiduously studied how to solve the problems noted above, and, as a result, have found the following: when an aromatic compound having a branched alkyl group with at least 3 carbon atoms is contacted with a zeolite-containing catalyst, then the position of the carbon atoms of the branched alkyl group bonding to the aromatic ring of the compound can be efficiently changed and, in addition, the loss of the alkyl group-substituted aromatic compound in the reaction is reduced and the catalyst activity is well protected from being lowered with the lapse of reaction time; when a halogenated aromatic compound having an alkyl group with at least 3 carbon atoms is contacted with an acid-type zeolite, then the compound can be efficiently isomerized; and when a mixture of isomers of an aromatic compound having an alkyl group with at least 3 carbon atoms is treated with an ion-exchanged zeolite adsorbent, then a specific isomer can be separated from the isomer mixture through adsorption. On the basis of these findings, we have completed the present invention.

Specifically, the invention is a method for producing aromatic compounds having an alkyl group with at least 3 carbon atoms, which comprises at least one of the following steps:

(1) a step of contacting a starting material that contains an aromatic compound having a branched alkyl group with at least 3 carbon atoms, with a zeolite-containing catalyst in a liquid phase in the presence of hydrogen therein, thereby changing the position of the carbon atoms of the alkyl group bonding to the aromatic ring of the compound;

(2) a step of contacting a starting material that contains an aromatic compound having a branched alkyl group with at least 3 carbon atoms, with a catalyst containing zeolite and containing rhenium and/or silver, in a liquid phase, thereby changing the position of the carbon atoms of the alkyl group bonding to the aromatic ring of the compound;

(3) a step of contacting a halogenated aromatic compound having an alkyl group with at least 3 carbon atoms, with an acid-type catalyst, thereby isomerizing the compound;

(4) a step of treating a mixture of isomers of an aromatic compound having an alkyl group with at least 3 carbon atoms, with a zeolite adsorbent that contains at least one exchangable cation selected from alkali metals, alkaline earth metals, lead, thallium and silver, thereby separating a specific isomer from the isomer mixture through adsorption.

According to the invention, a starting material that contains an aromatic compound having a branched alkyl group with at least 3 carbon atoms is contacted with (1) a zeolite-containing catalyst in, the presence of hydrogen, and/or (2) a catalyst containing zeolite and containing rhenium and/or silver, in a liquid phase, whereby the position of the carbon atoms of the alkyl group bonding to the aromatic ring of the compound can be efficiently changed, and, in addition, the loss of the alkyl group-substituted aromatic compound in the reaction is reduced and the catalyst activity is well protected from being lowered with the lapse of reaction time.

Also according to the invention, a halogenated aromatic compound having an alkyl group with at least 3 carbon atoms is isomerized through contact with zeolite, whereby a desired halogenated aromatic compound having an alkyl group with at least 3 carbon atoms can be efficiently obtained.

Still according to the invention, a mixture of isomers of an aromatic compound having an alkyl group with at least 3 carbon atom is treated with a zeolite adsorbent that contains at least one exchangable cation selected from alkali metals, alkaline earth metals, lead, thallium and silver, whereby a specific isomer of the aromatic compound having an alkyl group with at least 3 carbon atoms can be efficiently separated from the isomer mixture through adsorption.

DESCRIPTION OF THE PREFERRED EMBODIMENTS

Figure 1:
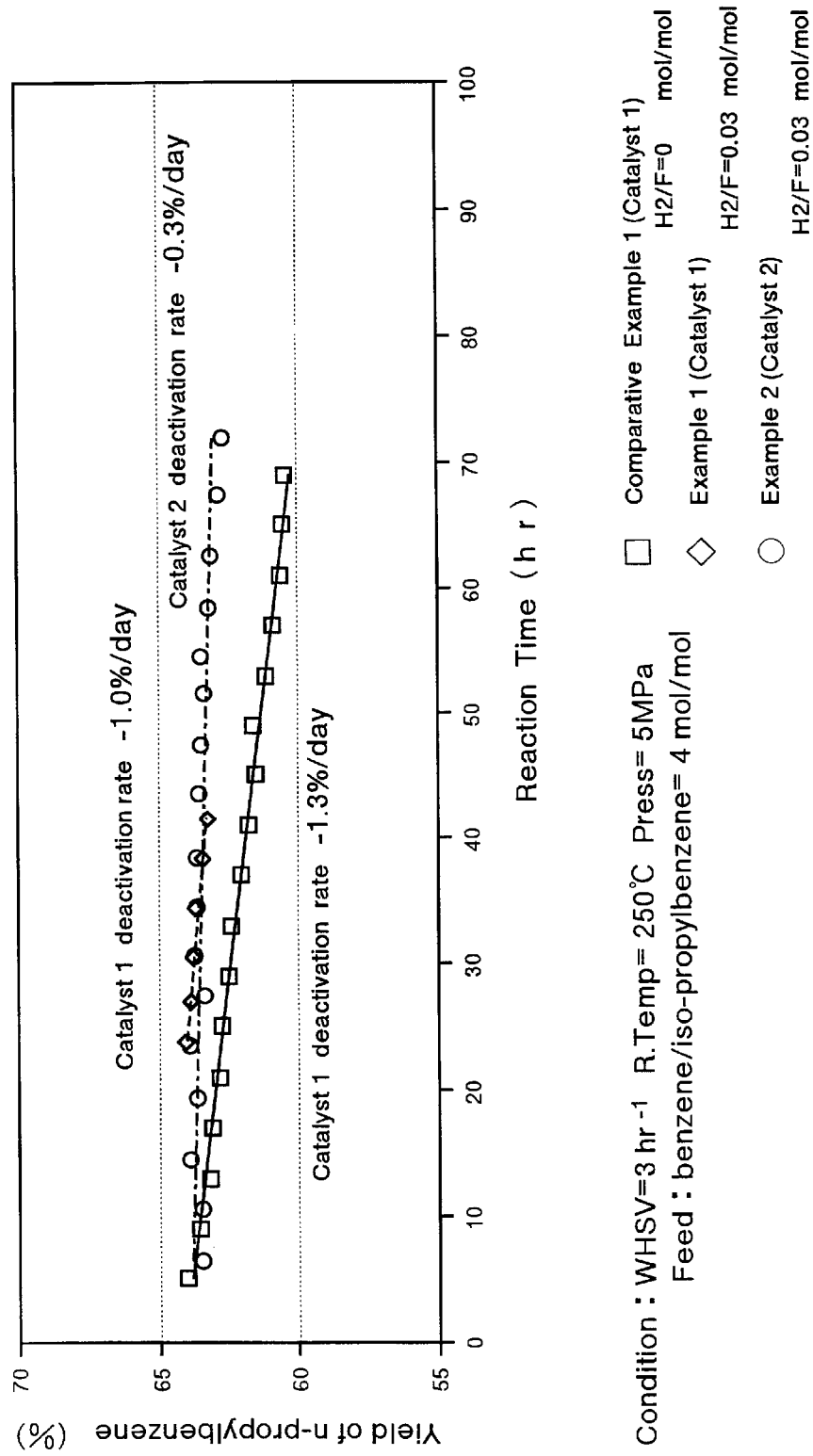
FIG. 1 is a graph showing the yield of n-propylbenzene versus reaction time in Examples 1 and 2 and Comparative Example 1.

Changing of the position of carbon atoms of alkyl group bonding to aromatic ring:

The aromatic compound having a branched alkyl group with at least 3 carbon atoms referred to herein is meant to indicate any and every one but excepting those in which the alkyl group has a linear carbon chain. In the compound, at least one carbon chain of the alkyl group shall be branched, and the alkyl group may have any hetero atoms. The hetero atoms include nitrogen, oxygen, sulfur and halogen atoms.

In the aromatic compound having a branched alkyl group with at least 3 carbon atoms to which the method of the invention is favorably applied, the alkyl group preferably has from 3 to 15 carbon atoms, more preferably from 3 to 8 carbon atoms. Except for the alkyl group, the compound may have at least one or more other substituents. The additional substituents include, for example, a methyl group, an ethyl group, a propyl group, a butyl group, a pentyl group, a halogen atom, a formyl group, a carboxyl group, an alkoxy group, a nitro group, an amino group, an amido group, a hydroxyl group, a cyano group, and an acayl group. The aromatic ring of the aromatic compound having a branched alkyl group with at least 3 carbon atoms includes, for example, a benzene ring, a naphthalene ring, a phenanthrene ring, and an anthracene ring, but preferred is a benzene ring.

Concretely, the aromatic compound includes, for example, isopropylbenzene, isopropyltoluene, isopropylethylbenzene, diisopropylbenzene, isopropylchlorobenzene, isopropylbromobenzene, isopropyldichlorobenzene, isopropyldibaromobenzene, isopropylnitrobenzene, isopropylanisole, isopropyldiphenyl ether, isopropylbenzonitrile, isopropylbenzoic acid, isopropylbenzaldehyde, isopropylbenzyl alcohol, isopropylphenol, sec-butylbenzene, sec-butyl toluene, sec-butylethylbenzene, sec-butylisopropylbenzene, disecbutylbenzene, sec-butylchlorobenzene, sec-butylbromobenzene, sec-butyldichlorobenzene, sec-butyldibromobenzene, sec-butylnitrobenizene, sec-butylanisole, sec-butyldiphenyl ether, sec-butylbenzoanitrile, sec-butylbenzoic acid, sec-butylbenzaldehyde, sec-butylbenzyl alcohol, sec-butylphenol, isobutylbenzene, isobutyltoluene, isobutylethylbenzenea, isobutylisopropylbenzene, diisobutylbenzene, isobutylchlorobaenzene, isobutylbromobenzene, iobutyldichlorobenzene, isobutyldibromobenzene, isobutylnitrobenzene, isobutylanisole, isobutyldiphenyl ether, isobutylbenzonitrile, isobutylbenzoic acid, isobutylbenzaldehyde, isobutylbenzyl alcohol, isobutylphenol, tert-butylbenzene, tert-butyltoluene, tert-butylethylbenzene, tert-butylisopropylbenzene, ditert-butylbenzene, tert-butylchlorobenzene, tert-butylbromobenzene, tert-butyldichlorobenzene, tert-butyldibromobenzene, tert-butylnitrobenzene, tert-butylanisole, tert-butyldiphenyl ether, tert-butylbenzonitrile, tert-butylbenzoic acid, tert-butylbenzaldehyde, tert-butylbenzyl alcohol, tert-butylphenol, isopentylbenzene, isopentyltoluene, isopentylethylbenzene, isopentylisopropylbenzene, diisopropylbenzene, isopentylchlorobenzene, isopentyldichlcorobenzene, isopentylnitrobenzene, isopentylanisole, isopentyldiphenyl ether, isopentylbenzonitrile, isopentylbenzoic acid, isopentylbenzaldehyde, isopentylbenzyl alcohol, isopentylphenol, neopentylbenzene, neopentylbenzene, neopentyltoluene, neopentylethylbenzene, neopentylisopropylbenzene, dineopentylbenzene, neopentylchlorobenzene, neopentyldichlorobenzene, neopentylnitrobenzene, neopentylanisole, neopentyldiphenyl ether, neopentylbenzonitrile, neopentylbenzoic acid, neopentylbenzaldehyde, neopentylbenzyl alcohol, neopentylphenol, sec-hexylbenzene, sec-hexyltoluene, sec-hexylethylbenzene, sec-hexylisopropylbenzene, disec-hexylbenzene, sec-hexylchlorobenzene, sec-hexyldichlorobenzene, sec-hexylnitrobenzene, sec-hexylanisole, sec-hexyldiphenyl ether, sec-hexylbenzonitrile, sec-hexylbentoic acid, sec-hexylbenzaldehyde, sec-hexylbenzyl alcohol, sec-hexylphenol, sec-heptylbenzene, sec-heptyltoluene, sec-heptylethylbenzene, sec-heptylisopropylbenzene, disec-heptylbenzene, sec-heptylchlorobenzener sec-heptyldichlorobenzene, sec-heptylnitrobenzene, sec-heptylanisole, sec-heptyldiphenyl ether, sec-heptylbenzonitrile, sec-heptylbenzoic acid, sec-heptylbenzaldehyde, sec-heptylbenzyl alcohol, sec-heptylphenol, sec-octylbenzene, sec-octyltoluene, sec-octylethylbenzene, sec-octylisopropylbenzene, disec-octylbenzene, sec-octylchlorobenzene, sec-octyldichlorobenzene, sec-octylnitrobenzene, sec-octylanisole, sec-octyldiphenyl ether, sec-octylbenzonitrile, sec-octylbenzoic acid, sec-octylbenzaldehyde, sec-octylbenzyl alcohol, sec-octylphenol, isopropylnaphthalene, and diisopropylnaphthalene.

Zeolite for use in the invention is not specifically defined, but preferred are faujasite-type, mordenite-type, beta-type and MFI-type zeolites. More preferred is MFI-type zeolite.

In the method of the invention, zeolite to be used is preferably of an acid type. As well known, zeolite of an acid type has, as cations, protons or divalent or higher polyvalent cations. In general, it may be prepared from zeolite having monovalent alkali metal ions such as sodium ions, by ion-exchanging at least a part of the alkali metal ions therein with protons or polyvalent cations, or by ion-exchanging them with ammonium cations capable of being converted into protons, followed by calcination of the thus-ion-exchanged zeolite. Ion-exchanging zeolite with the cations may be effected in any known manner. For example, the starting zeolite is processed with an aqueous solution of an acid, an ammonium salt or a water-soluble salt of a polyvalent cation, whereby it is readily ion-exchanged. Where zeolite has organic nitrogen-containing cations, it may be converted into an acid-type zeolite by calcination. Needless-to-say, if desired, it may also be subjected to any known ion-exchanging treatment whereby the alkali metal ions such as sodium ions originally existing therein may be further ion-exchanged with protons or ammonium cations, or divalent or higher polyvalent cations may be introduced into it. Anyhow, in the method of the invention, the type and the amount of zeolite to be used are not specifically defined.

In the method of the invention, zeolite to be used is generally a shaped one. The method for shaping zeolite is not specifically defined. Zeolite for use in the invention may be shaped in any known manner of, for example, rolling granulation, compression or extrusion. If desired, a binder such as alumina sol or clay maybe added to zeolite being shaped. Zeolite may be subjected to ion-exchanging treatment in any desired stage before and after shaping it. The shaped zeolite is activated by calcination generally at a temperature falling between 300 and 700° C., and is formed into a catalyst to be used herein.

The catalyst for use herein preferably contains at least one of rhenium and silver.

Rhenium maybe introduced into the catalyst, for example, through dipping or kneading. The condition of rhenium existing in the catalyst is not specifically defined. For example, rhenium may be in the catalyst in the form of the metal itself, or in the form of its compound, such as oxide, chloride, sulfide or selenide. It is desirable that the rhenium content of the catalyst is from 0.001% by weight to 5% by weight of the entire catalyst, as calculated in terms of the rhenium atom in any condition of rhenium in the catalyst. More preferably, it is from 0.005% by weight to 1.0% by weight.

The source of rhenium includes, for example, perrhenic acid, ammonium perrhenate, and rhenium chloride, which, however, are not limitative.

Silver may be introduced into the catalyst, for example, through ion-exchanging, dipping or kneading. The condition of silver existing in the catalyst is not specifically defined. For example, silver may be in the catalyst in the form of the metal itself, or in the form of its compound, such as oxide, chloride, sulfide or selenide. It is desirable that the silver content of the catalyst is from 0.1% by weight to 15% by weight of the entire catalyst, as calculated in terms of the silver atom in any condition of silver in the catalyst. More preferably, it is from 0.2% by weight to 10% by weight.

When silver is introduced into the zeolite component for the catalyst through ion-exchanging, the ion-exchanging treatment is generally effected in an aqueous solution. Therefore, it is desirable that the silver compounds to be used for the ion-exchanging treatment are soluble in water. One example of water-soluble silver compounds is silver nitrate.

Like such ion-exchanging treatment, silver dipping is also effected generally in an aqueous solution. Therefore, water-soluble silver compounds such as silver nitrate are used for the dipping method.

On the other hand, the silver compounds to be applied to zeolite through kneading are not always required to be soluble in water. Water-insoluble compounds such as silver sulfide, silver chloride or silver carbonate may also be used for the kneading method.

Of those methods, ion-exchanging treatment is preferred as silver can be uniformly dispersed in zeolite through it.

In order to prevent the activity of the catalyst from being lowered with the lapse of reaction time, it is desirable to previously sulfurate the catalyst before it is used for catalyzation. For the sulfuration, the catalyst is contacted with a solution or vapor that contains a sulfur compound.

One effect of the sulfuration is that sulfur reacts with rhenium or silver in the catalyst to form rhenium or silver sulfide therein, thereby enhancing the dispersibility of the metallic component in the catalyst and enhancing the hydrogenation capabilities of the metallic component.

The sulfur compound is not specifically defined, including, for example, carbon disulfide, hydrogen disulfide thiophene, dimethyl sulfoxide, dimethyl sulfone, dimethyl sulfide, methanethiol, ethanethiol, and thiophenol, etc.

The sulfuration maybe effected either in a liquid phase or in a vapor phase, but is preferably effected in a vapor phase in view of the easiness in the post-treatment of the processed catalyst. For example, preferred is a method of contacting the catalyst with a vapor system that contains a vapor of a sulfur compound.

Regarding the condition for the sulfuration for which is used a vapor system containing a vapor of a sulfur compound, the partial pressure of the sulfur compound vapor preferably falls between 0.0013 and 0.5 MPa.

The temperature for the treatment preferably falls between room temperature and 500° C., and the time for it preferably falls between 0.5 and 24 hours. However, these are not limitative.

The treatment may be effected after rhenium and/or silver are/is held on the carrier, and in any stage before, during or after the calcination at 300 to 700° C.

In order also to prevent the activity of the catalyst from being lowered with the lapse of reaction time, it is desirable to pre-treat the catalyst with steam before it is used for the reaction. For the steam treatment, the catalyst is contacted with a steam-containing vapor.

For the steam treatment, preferably, the catalyst is processed in a steam atmosphere. Regarding the condition for the steam treatment, the partial pressure of steam preferably falls between 0.0065 and 0.5 MPa, the temperature preferably falls between 200 and 700° C., and the time preferably falls between 0.5 and 24 hours.

If the partial pressure of steam is lower than 0.0065 MPa, or if the temperature is lower than 200° C., the effect of the steam treatment will be poor. On the other hand, if the partial pressure of steam is higher than 0.5 MPa or if the temperature is higher than 700° C., the activity of the catalyst will be rather lowered.

More preferably, the partial pressure of steam falls between 0.0065 and 0.1 MPa, and the temperature for the treatment falls between 500 and 600° C.

The steam treatment may be effected before or after rhenium and/or silver are/is held on the carrier, or in any stage before, during or after the calcination at 300 to 700° C.

After the steam treatment, it is desirable that the catalyst is processed in an aqueous solution containing at least one selected from hydrochloric acid, ethylenediamine-tetraacetic acid and tartaric acid. Through the treatment, side reaction sites that may cause dealkylation could be washed away from the catalyst, and the loss of the alkyl group-substituted aromatic compound in the reaction with the thus-washed catalyst could be reduced.

Ethylenediamine-tetraacetic acid and tartaric acid to be used for that purpose may be in the form of such a free acid or may also be in the form of their alkali metal salts or alkaline earth metal salts. However, preferred is the free acid of ethylenediamine-tetraacetic acid or tartaric acid.

In the method of the invention, a starting material that contains an aromatic compound having a branched alkyl group with at least 3 carbon atoms is, in a liquid phase, contacted with (1) the zeolite-containing catalyst thus prepared in the manner noted above, in the presence of hydrogen, and/or (2) the catalyst containing zeolite and containing rhenium and/or silver and having been prepared in the manner noted above, whereby the positions of the carbon atoms of the alkyl group bonded to the aromatic ring of the compound are rearranged.

In the method of the invention, a starting material that contains an aromatic compound having a branched alkyl group with at least 3 carbon atoms is, in a liquid phase, contacted with (1) the zeolite-containing catalyst thus prepared in the manner noted above, in the presence of hydrogen, and/or (2) the catalyst containing zeolite and containing rhenium and/or silver and having been prepared in the manner noted above, whereby the position of the carbon atoms of the alkyl group bonding to the aromatic ring of the compound is changed.

In the invention, it is desirable that the reaction system additionally contains any other aromatic compound that differs from the aromatic compound having a branched alkyl group with at least 3 carbon atoms to be in the system. The additional aromatic compound may be either unsubstituted or substituted, but must have at least one hydrogen bonding to its aromatic ring. For example, it includes benzene, naphthalene, phenanthrene, anthracene, toluene, ethylbezene, chlorobenzene, dichlorobenzene, trichlorobenzene, chlorotoluene, dichlorotoluene, bromobenzene, dibromobenzene, bromotoluene, dibromotoluene, bromochlorobenzene, benzoic acid, benzaldehyde, nitrobenzene, aniline, anisole, phenol, and benzonitrile, but is not limited to these. The ratio of the additional aromatic compound to the aromatic compound having a branched alkyl group with at least 3 carbon atoms is preferably from 1/20 to 20/1 (mol/mol). The ratio of the additional aromatic compound to the aromatic compound having a branched alkyl group with at least 3 carbon atoms of being not smaller than 1/20 (mol/mol) is preferred, as the side reaction such as dealkylation of the aromatic compound having a branched alkyl group with at least 3 carbon atoms could be well prevented in that range; and the ratio of being not larger than 20/1 (mol/mol), is also preferred, as the concentration of the intended product produced in the reaction liquid could be kept high.

The details of the mechanism are not clear as to why the position of the carbon atoms of the alkyl group bonding to the aromatic ring of an aromatic compound having a branched alkyl group with at least 3 carbon atoms is rearranged in the method of the invention, but it is true that the additional aromatic compound which differs from the aromatic compound having a branched alkyl group with at least 3 carbon atoms and which is present in the reaction system along with the latter aromatic compound will surely have some influences on the reaction mechanism in a certain manner since the presence of the additional aromatic compound in the reaction system promotes the reaction. In this connection, it believed that, while me alkyl group in the aromatic compound having a branched alkyl group with at least 3 carbon atoms is transferred from the aromatic compound to the neighboring aromatic compound existing in the reaction system that contains zeolite (through transalkylation), the alkyl group will be converted into a different alkyl group of which the number of the branches is smaller than originally, and/or into a different alkyl group of which the branched chains are shorter than originally, and/or into a different alkyl group which bonds to the aromatic ring via its secondary carbon.

As so mentioned above, it is believed that the method of the invention is closely related with transalkylation between an aromatic compound having a branched alkyl group with at least 3 carbon atoms and a neighboring aromatic compound, and, in fact, the method of the invention can be carried out substantially in accordance with any known transalkylation of various conventional alkyl group-substituted aromatic compounds.

The method of the invention is for liquid-phase reaction. Needless-to-say, therefore, the reaction pressure in the method must be so appropriately controlled that the reaction system could be kept in a liquid-phase condition under the controlled pressure. If, in the method of the invention, the reaction is effected in a conventional vapor phase, high-boiling-point compounds such as dimers that may be formed in side reaction will deposit on the catalyst to greatly deactivate the catalyst. As opposed to this, in a liquid phase, the side products of such high-boiling-point compounds could be washed away from the catalyst by the reaction liquid. In that condition, therefore, the catalyst life is prolonged to an industrial level.

Where the method of the invention is carried out in such a liquid phase in the presence of hydrogen, the co-existing hydrogen will act to prevent the formation of the compounds that may deactivate the catalyst. In that condition, therefore, the catalyst activity can be kept high and the catalyst life can be much prolonged. The ratio by mol of the co-existing hydrogen to the starting material of the aromatic compound having a branched alkyl group with at least 3 carbon atoms or to the total mol of the starting material of the aromatic compound as combined with an additional aromatic compound, if any, that differs from the aromatic compound of the starting material may fall between 0.0001 and 1 mol/mol, but preferably between 0.001 and 0.1 mol/mol. Too much hydrogen, if existing in the reaction system, will be uneconomical. Therefore, the uppermost limit of the amount of the co-existing hydrogen shall be determined in consideration of the economic aspect. As a rule, hydrogen may be introduced into the reaction system to be not larger than its solubility therein.

For the method of the invention, employable is any reaction system for a fixed bed, a moving bed or a fluidized bed. For easy operation, preferred is a fixed-bed flow system.

The reaction temperature generally falls between 150 and 500° C., but preferably between 200 and 400° C.

The reaction pressure is not specifically defined, and may be normal pressure or may even be any desired, increased or reduced pressure. In order to increase the hydrogen dissolution therein, however, the reaction system is preferably pressurized. The preferred pressure range falls between 0.1 and 20 MPa.

The weight hourly space velocity (WHSV) that indicates the flow rate of the starting material being applied to the catalyst for the intended reaction may fall between 0.05 and 40 $hr^{-1}$, but preferably between 0.1 and 20 $hr^{-1}$, relative to the weight of the catalyst.

The intended product, aromatic compound as produced according to the method of the invention may be separated and purified through ordinary distillation, crystallization, chromatography, simulated moving bed adsorption. Where the non-reacted starting material is recovered, it may be fed back to the first reaction stage.

According to the method of the invention described above, the position of the carbon atoms of the branched alkyl group having at least 3 carbon atoms and bonding to the aromatic ring of an aromatic compound can be efficiently changed and, in addition, the loss of the alkyl group-substituted aromatic compound in the reaction is small and the catalyst activity is well protected from being lowered with the lapse of reaction time. Having these advantages, the method of the invention is extremely favorable to conversion of aromatic compounds.

For isomerization of halogenated aromatic compound having an alkyl group with at least 3 carbon atoms, the zeolite to be used in the method of the invention is not specifically defined, provided that it is an acid-type one. Preferred is zeolite having a pore size of at least 6 angstroms. Zeolite having a pore size of at least 6 angstroms includes, for example, mordenite-type, faujasite-type and beta-type zeolites. A method for producing faujasite-type zeolite is disclosed, for example, in Japanese Patent Publication No. 15400/1977; that for producing beta-type zeolite is, for example, in U.S. Pat. No. 3,308,069 and Japanese Patent Publication No. 223989/1995; and that for producing mordenite-type zeolite is, for example, in Japanese Patent Publication No. 46677/1972, Japanese Patent Laid-Open No. 26529/1980 and Japanese Patent Publication No. 31006/1990.

Though not always indispensable, zeolite for use in the method of the invention is generally but preferably a shaped one. The method for shaping zeolite is not specifically defined. Zeolite for use in the invention may be shaped in any known manner of, for example, rolling granulation, compression or extrusion. If desired, a binder such as alumina sol or clay may be added to zeolite being shaped. The shaped zeolite is activated by calcination generally at a temperature falling between 300 and 700° C., and is formed into a catalyst to be used herein.

Where the zeolite catalyst is used for isomerization in the invention, it shall be an acid-type one, as a rule. As well known, an acid-type zeolite can be obtained by ion-exchanging the cations in zeolite with hydrogen ions or divalent or higher poly-valent cations. Exchanging the cations in zeolite with hydrogen ions is preferred, as the resulting zeolite could have higher activity.

For exchanging the cations in zeolite with hydrogen ions, generally employed is a method of directly ion-exchanging zeolite in an aqueous solution of an acid; or a method of exchanging the metal cations in zeolite with ammonium ions followed by calcination of the thus-processed zeolite. Where the starting zeolite has organic nitrogen-containing cations, it may be calcined whereby the organic nitrogen-containing cations therein may be decomposed and converted into hydrogen ions. In that manner, zeolite can be converted into an acid-type one.

In the halogenated aromatic compound having an alkyl group with at least 3 carbon atoms, which is processed according to the method of the invention, the halogen may be in any position of ortho (o-), meta (m-) and para (p-) positions relative to the alkyl group bonding to one and the same aromatic ring of the compound. The halogen may be, for example, chlorine or bromine, and the compound may have two or more halogens on one aromatic ring of the compound. The starting material to be isomerized in the invention may be any of a single isomer or a mixture of different isomers. In the invention, any type of isomers may be isomerized with no problem. The aromatic compound having an alkyl group with at least 3 carbon atoms may have any hetero atoms in the alkyl group. The hetero atoms include nitrogen, oxygen, sulfur and halogen atoms. Specific examples of the halogenated aromatic compound having an alkyl group with at least 3 carbon atoms include o-chloroisopropylbenzene, o-chloro-n-propylbenzene, m-chloroisopropylbenzene, m-chloro-n-propylbenzene, p-chloroisopropylbenzene, p-chloro-n-propylbenzene, o-bromoisopropylbenzene, o-bromo-n-propylbenzene, m-bromoisopropylbenzene, m-bromo-n-propylbenzene, p-bromoisopropylbenzene, p-bromo-n-propylbenzene, 1,3-dichloro-4-isopropylbenzene, 1,3-dichloro-4-n-propylbenzene, 1,3-dichloro-5-isopropylbenzene, 1,3-dichloro-5-n-propylbenzene, 1-chloro-2,4-diisopropylbenzene, 1-chloro-2,4-di-n-propylbenzene, o-chloroisobutylbenzene, o-chloro-n-butylbenzene, m-chloroisobutylbenzene, m-chloro-n-butylbenzene, p-chloroisobutylbenzene, p-chloro-n-butylbenzene, o-bromoisobutylbenzene, o-bromo-n-butylbenzene, m-bromoisobutylbenzene, m-bromo-n-butylbenzene, p-bromo-isobutylbenzene, p-bromo-n-butylbenzene, 1,3-dichloro-4-isobutylbenzene, 1,3-dichloro-4-n-butylbenzene, 1,3-dichloro-5-isobutylbenzene, 1,3-dichloro-5-n-butylbenzene, 1-chloro-2,4-diisobutylbenzene, 1-chloro-2,4-di-n-butylbenzene, o-chloro-sec-butylbenzene, m-chloro-sec-butylbenzene, p-chloro-sec-butylbenzene, o-bromo-sec-butylbenzene, m-bromo-sec-butylbenzene, p-bromo-sec-butylbenzene, 1,3-dichloro-4-sec-butylbenzene, 1,3-dichloro-5-sec-butylbenzene, and 1-chloro-2,4-di-sec-butylbenzene.

In the invention, the reaction may be attained in any system of a flow process or a batch process. The reaction may be attained under heating, and the temperature for it generally falls between 100° C. and 500° C., but preferably between 150° C. and 400° C. The reaction pressure is not specifically defined, and may be normal pressure or may even be any desired, increased or reduced pressure. The weight hourly space velocity (WHSV) that indicates the flow rate of the starting material being applied to the catalyst for the intended reaction may fall generally between 0.01 and 50 hr$^{-1}$, but preferably between 0.1 and 10 hr$^{-1}$, relative to the weight of the catalyst.

In the method of the invention, the starting material, halogenated aromatic compound having an alkyl group with at least 3 carbon atoms may be diluted with a different halogenobenzene and/or benzene. The ratio by weight of the diluent to the starting material may fall generally between 1/20 and 20/1 (wt/wt), but preferably between 1/5 and 5/1 (wt/wt).

In the method of the invention, it is desirable that hydrogen exists in the reaction system. The amount of hydrogen to be in the system generally falls between 0.01 and 40 mol %, but preferably between 1 and 25 mol %, based on the starting material, halogenated aromatic compound having an alkyl group with at least 3 carbon atoms.

Preferably, the catalyst for use in the invention contains at least one metal selected from metals of Groups 7 to 11 of the Periodic Table. The metal includes, for example, silver and copper of Group 11, rhenium of Group 7, and iron, nickel and platinum of Groups 8 to 10. Especially preferred is silver or rhenium. Introducing the metal into the catalyst may be attained, for example, through dipping, ion-exchanging or kneading. As the metal source, preferred are water-soluble compounds of the metal such as hydrochlorides, nitrates or oxides thereof, as the metal from them could be well dispersed in the catalyst. In any case, the amount of the metal to be in the catalyst may fall between 0.01% by weight and 5.0% by weight, but preferably between 0.01% by weight and 1.0% by weight, in terms of the weight of the metal atom relative to the total weight of the catalyst.

Diluting the starting material with the diluent noted above, or introducing hydrogen into the reaction system, and also introducing the metal into the catalyst are all effective for reducing the loss of the starting material, halogenated aromatic compound having an alkyl group with at least 3 carbon atoms owing to the side reaction such as disproportionation of the compound, and for preventing the deactivation of the catalyst.

As described above, efficient isomerization of a halogenated aromatic compound having an alkyl group with at least 3 carbon atoms is possible according to the method of the invention in which the alkyl group of the compound is well prevented from dealkylated from the aromatic ring of the compound.

Adsorptive separation:

The expression "aromatic compound having an alkyl group with at least 3 carbon atoms", which is processed according to the method of the invention, is meant to indicate any and every one where the carbon chain of the alkyl group bonding to its aromatic ring has at least 3 carbons continuously bonding to each other in series. In the compound, the alkyl group may include any hetero atoms. The hetero atoms include nitrogen, oxygen, sulfur and halogen atoms.

In the aromatic compound having an alkyl group with at least 3 carbon atoms to which the method of the invention is favorably applicable, the alkyl group preferably has from 3 to 8 carbon atoms, more preferably from 3 to 6 carbon atoms. The alkyl group may be either linear or branched. As the case may be, the compound may be mixture of such linear and/or branched alkyl groups, and may have any one or more other substituents in addition to the alkyl group. The substituents include, for example, a methyl group, an ethyl group, a propyl group, a butyl group, a pentyl group, a hexyl group, a heptyl group, an octyl group, a phenyl group, a halogen atom, a formyl group, a carboxyl group, an acyl group, an alkoxy group, a nitro group, an amino group, an amido group, a hydroxyl group, and a cyano group. The propyl, butyl, pentyl, hexyl, heptyl and octyl groups may be linear or branched. In particular, compounds having any of a methyl group, an ethyl group, a propyl group, a phenyl group and a halogen atom are preferred, as they have many industrial applications and the method of the invention applied to those compounds produces great economic effects.

The aromatic ring of the aromatic compound having an alkyl group with at least 3 carbon atoms includes, for example, a benzene ring, a naphthalene ring, a phenanthrene ring, and an anthracene ring, but preferred is a benzene ring. Concretely, the aromatic compound includes, for example, alkylbenzenes, halogenoalkylbenzenes, dialkylbenzenes, alkylbenzaldehydes, alkylbenzoic acids, alkylacetophenones, alkylpropiophenones, alkoxyalkylbenzenes, alkylnitrobenzenes, alkylanilines, alkylbenzylamines, alkylbenzamides, alkylphenols, alkylbenzyl alcohols, alkylbenzonitriles, and alkylnaphthalenes.

Specific examples of the alkylbenzenes for the aromatic compound having an alkyl group with at least 3 carbon atoms include propylbenzene, butylbenzene, pentylbenzene, hexylbenzene, heptylbenzene, and octylbenzene; those of the halogenoalkylbenzenes for it include fluoropropylbenzene, chloropropylbenzene, bromopropylbenzene, iodopropylbenzene, dichloropropylbenzene, dibromopropylbenzene, fluorobutylbenzene, chlorobutylbenzene, bromobutylbenzene, iodobutylbenzene, dichlorobutylbenzene, dibromobutylbenzene, fluoropentylbenzene, chloropentylbenzene, bromopentylbenzene, iodopentylbenzene, dichloropentylbenzene, dibromopentylbenzene, fluorohexylbenzene, chlorohexylbenzene, bromohexylbenzene, iodohexylbenzene, dichlorohexylbenzene, dibromohexylbenzene, fluoroheptylbenzene, chloroheptylbenzene, bromoheptylbenzene, iodoheptylbenzene, dichloroheptylbenzene, dibromoheptylbenzene, fluorooctylbenzene, chlorooctylbenzene, bromooctylbenzene, iodooctylbenzene, dichlorooctylbenzene, and dibromooctylbenzene. In these, the alkyl group may be linear or branched.

Specific examples of the dialkylbenzenes include propyltoluene, ehtylpropylbenzene, dipropylbenzene, butylpropylbenzene, pentylpropylbenzene, hexylpropylbenzene, heptylpropylbenzene, octylpropylbenzene, propyldihenyl, butyltoluene, butylethylbenzene, dibutylbenzene, butylpentylbenzene, butylhexylbenzene, butylheptylbenzene, butyloctylbenzene, butyldiphenyl, pentyltoluene, ethylpentylbenzene, dipentylbenzene, hexylpentylbenzene, heptylpentylbenzene, octylpentylbenzene, pentyldiphenyl, hexyltoluene, ethylhexylbenzene, dihexylbenzene, heptylhexylbenzene, hexyloctylbenzene, hexyldiphenyl, heptyltoluene, ethylheptylbenzene, diheptylbenzene, heptyloctylbenzene, heptyldiphenyl, octyltoluene, ethyloctylbenzene, dioctylbenzene, and octyldiphenyl; and those of the alkylbenzaldehydes include propylbenzaldehyde, butylbenzaldehyde, pentylbenzaldehyde, hexylbenzaldehyde, heptylbenzaldehyde, and octylbenzaldehyde. In these, the alkyl group may be linear or branched.

The alkylbenzoic acids include, for example, propylbenzoic acid, butylbenzoic acid, hexylbenzoic acid, heptylbenzoic acid, and octylbenzoic acid; the alkylacetophenones include, for example, propylacetophenone, butylacetophenone, pentylacetophenone, hexylacetophenone, heptylacetophenone, and octylacetopheonone; the alkylpropiophenones include, for example, propylpropiophenone, butylpropiophenone, pentylpropiophenone, hexylpropiophenone, heptylpropiophenone, and octylpropiophenone; and the alkoxyalkylbenzenes include, for example, propylanisole, butylanisole, pentylanisole, hexylanisole, heptylanisole, octylanisole, propylphenetole, butylphenetole, pentylphenetole, hexylphenetole, heptylphenetole, octylphenetole, propylphenoxybenzene, butylphenoxybenzene, pentylphenoxybenzene, hexylphenoxybenzene, heptylphenoxybenzene, and octylphenoxybenzene. In these, the alkyl group may be linear or branched.

The alkylnitrobenzenes include, for example, propylnitrobenzene, butylnitrobenzene, pentylnitrobenzene, hexylnitrobenzene, heptylnitrobenzene, and octylnitrobenzene; the alkylanilines include, for example, propylaniline, butylaniline, pentylaniline, hexylaniline, heptylaniline, and octylaniline; the alkylbenzylamines include, for example, propylbenzylamine, butylbenzylamine, pentylbenzylamine, hexylbenzylamine, heptylbenzylamine, and octylbenzylamine; and the alkylbenzamides include, for example, propylbenzamide, butylbenzamide, pentylbenzamide, hexylbenzamide, heptylbenzamide, and octylbenzamide. In these, the alkyl group may be linear or branched.

The alkylphenols include, for example, propylphenol, butyl phenol, pentylphenol, hexylphenol, and heptylphenol, octylphenol; the alkylbenzyl alcohols include, for example, propylbenzyl alcohol, butylbenzyl alcohol, pentylbenzyl alcohol, hexylbenzyl alcohol, heptylbenzyl alcohol, and octylbenzyl alcohol; and the alkylbenzonitriles include, for example, propylbenzonitrile, butylbenzonitrile, pentylbenzonitrile, hexylbenzonitrile, heptylbenzonitrile, and octylbenzonitrile. In these, the alkyl group may be linear or branched.

The alkylnaphthalenes include, for example, propylnaphthalene, butylnaphthalene, pentylnaphthalene, hexylnaphthalene, heptylnaphthalene, octylnaphthalene, chloropropylnaphthalene, chlorobutylnaphthalene, chloropentylnaphthalene, chlorohexylnaphthalene, chloroheptylnaphthalene, chlorooctylnaphthalene, dichloropropylnaphthalene, dichlorobutylnaphthalene, dichloropentylnaphthalene, dichlorohexylnaphthalene, dichloroheptylnaphthalene, dichlorooctylnaphthalene, bromopropylnaphthalene, bromobutylnaphthalene, bromopentylnaphthalene, bromohexylnaphthalene, bromoheptylnaphthalene, bromooctylnaphthalene, dibromopropylnaphthalene, dibromobutylnaphthalene, dibromopentylnaphthalene, dibromohexylnaphthalene, dibromoheptylnaphthalene, dibromooctylnaphthalene, bromochloropropylnaphthalene, bromochlorobutylnaphthalene, bromochloropentylnaphthalene, bromochlorohexylnaphthalene, bromochloroheptylnaphthalene, and bromochlorooctylnaphthalene. In these, the alkyl group may be linear or branched.

The alkyl group having at least 3 carbon atoms includes, for example, an n-propyl group, an iso-propyl group, an n-butyl group, an isobutyl group, a sec-butyl group, a tert-butyl group, an n-pentyl group, an isopentyl group, a neopentyl group, a sec-pentyl group, a tert-pentyl group, an n-hexyl group, an isohexyl group, a sec-hexyl group, and a tert-hexyl group. Of those, n-alkyl groups of, for example, n-propyl, n-butyl, n-pentyl and n-hexyl groups, as well as sec-alkyl groups of, for example, sec-butyl, sec-pentyl and sec-hexyl groups are important, as aromatic compounds with any of those groups have diverse applications.

According to the technique of the invention, c-, m- and p-isomers can be separated. In general, o- and p-isomers are readily produced in direct alkylation and halogenation on aromatic rings. Therefore, the technique of the invention is especially useful for obtaining m-isomers.

The object of the invention is to separate the compounds described as above. In particular, the compounds to which the invention is favorably applied are o-chloro-n-propylbenzene, m-chloro-n-propylbenzene, p-chloro-n-propylbenzene, o-chloro-isopropylbenzene, m-chloro-isopropylbenzene, p-chloro-isopropylbenzene, o-bromo-n-propylbenzene, m-bromo-n-propylbenzene, p-bromo-n-propylbenzene, o-bromo-isopropylbenzene, m-bromo-isopropylbenzene, p-bromo-isopropylbenzene, o-iodo-n-propylbenzene, m-iodo-n-propylbenzene, p-iodo-n-propylbenzene, o-iodo-isoproylbenzene, m-iodo-isopropylbenzene, o-iodo-isopropylbenzene, o-chloro-n-butylbenzene, m-chloro-n-butylbenzene, p-chloro-n-butylbenzene, o-chloro-isobutylbenzene, m-chloro-isobutylbenzene, p-chloro-isobutylbenzene, o-chloro-secbutylbenzene, m-chloro-sec-butylbenzene, p-chloro-sec-butylbenzene, o-chloro-tert-butylbenzene, m-chloro-tert-butylbenzene, p-chloro-tert-butylbenzene, o-bromo-n-butylbenzene, m-bromo-n-butylbenzene, p-bromo-n-butylbenzene, o-bromo-isobutylbenzene, m-bromo-isobutylbenzene, p-bromo-isobutylbenzene, o-bromo-sec-butylbenzene, m-bromo-sec-butylbenzene, p-bromo-sec-butylbenzene, o-bromo-tert-butylbenzene, m-bromo-tert-butylbenzene, p-bromo-tert-butylbenzene, o-iodo-n-butylbenzene, m-iodo-n-butylbenzene, p-iodo-n-butylbenzene, o-iodo-isobutylbenzene, m-iodo-isobutylbenzene, p-iodoisobutylbenzene, o-iodo-sec-butylbenzene, m-iodo-sec-butylbenzene, p-iodo-sec-butylbenzene, o-iodo-tert-butylbenzene, m-iodo-tert-butylbenzene, and p-iodo-tert-butylbenzene. Of those, more favorably, the invention is applied to m-chloro-n-propylbenzene, m-chloro-isopropylbenzene, m-bromo-n-propylbenzene, m-bromo-isopropylbenzene, m-chloro-n-butylbenzene, m-chloro-sec-butylbenzene, m-bromo-n-butylbenzene, and m-bromo-sec-butylbenzene.

In the invention, the zeolite adsorbent contains at least one exchangeable cation selected from alkali metals, alkaline earth metals, lead, thallium and silver.

The alkali metals include, for example, lithium, sodium, potassium, cesium, and rubidium; and the alkaline earth metals include, for example, magnesium, calcium, strontium, and barium.

The exchangable cations in zeolite can be replaced by various cations through ion-exchanging. The cation-exchanging may be effected by contacting zeolite with a compound having intended cations, for example, with any of hydrochlorides, nitrates, sulfates, carbonates or hydroxides in their aqueous solutions. The degree of cation-exchanging varies, depending on the type of the cation, but may be suitably determined by controlling the concentration of the aqueous solution to be used for ion-exchanging. For silver ion-exchanging, for example, it is desirable that zeolite is processed in an aqueous solution having a silver content of from 0 to 50% of the ion-exchanging site in zeolite, but more preferably in an aqueous solution having a silver content of from 2 to 20% thereof. After having been processed for the intended ion-exchanging, zeolite is well washed with water to remove therefrom sodium ions and other ions of, for example, chloride ions and nitrate ions having been released in the aqueous solution through the ion-exchanging treatment.

Zeolite for use in the invention is not specifically defined, but is preferably selected from faujasite-type, pentacyl-type, mordenite-type and beta-type zeolites. More preferred is faujasite-type zeolite.

Zeolite for use in the invention may be a so-called, isomorphoursly substituted zeolite, which may be prepared by substituting a part of silica (or silicon) that constitutes zeolite with germanium or by substituting a part of aluminium with any of gallium, chromium or iron.

Zeolite for use in the invention may be any of synthetic ones or commercially-available ones. Synthetic zeolites may be produced in any known manner. For example, U.S. Pat. Nos. 2,882,244 and 3,130,007 disclose a method of producing faujasite-type zeolite; and U.S. Pat. Nos. 3,702,866 and 4,511,547 disclose a method of producing pentacyl-type zeolite.

Faujasite zeolite preferred in the invention includes X-type zeolite and Y-type zeolite, which are crystalline aluminosilicates of the following formula:

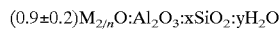

$(0.9\pm0.2)M_{2/n}O:Al_2O_3:xSiO_2:yH_2O$

In the formula, M represents a cation, and n indicates the valence of the cation M. x generally falls between 2 and 6 for faujasite zeolite. Faujasite zeolite is grouped into two types; one is X-type zeolite with x of from 2 to 3, and the other is Y-type zeolite with x of from 3 to 6. y differs, depending on the degree of hydration of the compound.

The adsorbent for use in the invention may be a solid of zeolite alone, or may also be in the form of granules as formed through granulation of zeolite with a binder of, for example, silica, alumina, silica-alumina, magnesia or other clay minerals.

If desired, zeolite for use in the invention may be in the form of a mixture of two or more different types of zeolite.

The adsorbent for use in the invention is preferably pre-treated for removing crystal water from zeolite therein. In general, it may be heated at a temperature falling between 200 and 600° C. whereby almost all crystal water could be removed from it.

For adsorbing and separating a mixture of isomers of an alkyl group-substituted aromatic compound according to the adsorptive separation technique of the invention of using the adsorbent as above, employable is any of so-called partitioning chromatography or simulated moving bed adsorption for which a cycle of partitioning chromatography is continuously repeated.

The basic process of continuous adsorptive separation in a simulated moving bed system comprises a cycle of adsorption, concentration and desorption mentioned below, and the cycle is continuously repeated for simulated moving bed adsorption.

(1) Adsorption step:

A starting material that contains a mixture of isomers of an alkyl group-substituted aromatic compound is contacted with the adsorbent of the invention, whereby the adsorbent selectively adsorbs the component in the mixture that is most strongly adsorbed by it. The most most strongly-adsorbed component is recovered as the extract along with the desorbent to be mentioned below.

(2) Concentration step:

The remaining raffinate that contains most of the weakly-adsorbable component is further contacted with the adsorbent, whereby the most most strongly-adsorbable component therein is selectively adsorbed by the adsorbent. As a result, the weakly-adsorbable component in the raffinate is purified to have a higher purity.

(3) Desorption step:

The thus-purified, weakly-adsorbable component is recovered as the raffinate, while the most most strongly-adsorbed component is removed from the adsorbent by the action of a desorbent and is recovered as the extract along with the desorbent.

As the desorbent for the adsorptive separation as above, preferred are alkyl-substituted aromatic hydrocarbons, halogenated aromatic hydrocarbons, or halogenated, alkyl-substituted aromatic hydrocarbons.

Specific examples of the alkyl-substituted aromatic hydrocarbons include toluene, ethylbenzene, xylene, propylbenzene, trimethylbenzene, diethylbenzene, and tetramethylbenzene.

Specific examples of the halogenated aromatic hydrocarbons include chlorobenzene, dichlorobenzene, and trichlorobenzene. Specific examples of the halogenated, alkyl-substituted aromatic hydrocarbons include chlorotoluene, dichlorotoluene, and chloroxylene.

Of those desorbents noted above, preferred are chlorotoluene, chlorobenzene and xylene. More preferably, at lease one selected from o-chlorotoluene, p-chlorotoluene, o-xylene and m-xylene is used.

These desorbents may be used either singly or as combined.

Regarding the condition for the adsorptive separation, the temperature preferably falls between room temperature and 350° C., more preferably between 50 and 250° C., and the pressure preferably falls between atmospheric pressure and 4 MPa, more preferably between atmospheric pressure and 3 MPa. In the invention, the adsorptive separation may be effected even in a vapor phase, for which, however, a liquid phase is preferred. In liquid-phase adsorptive separation, the temperature may be lowered to prevent conversion of the starting material or the desorbent and to prevent deactivation of the adsorbent.

In the invention where a p-halogeno-n-alkylbenzene is separated as the extract component, preferably used is pentacyl-type zeolite having an alkali metal cation, or Y-type or Y-type zeolite having at least one cation selected from alkali metals, alkaline earth metals, lead, thallium and silver. More preferred is pentacyl-type zeolite having lithium and/or sodium, or X-type or Y-type zeolite having potassium and/or barium. As the cation, especially preferred are sodium and barium. As the desorbent, concretely, preferred are chlorotoluene and chlorobenzene, and more preferred is o-chlorotoluene.

In the invention where an m-halogeno-n-alkylbenzene is separated as the extract component, preferably used is X-type or Y-type zeolite having at least one cation selected from alkali metals, alkaline earth metals, lead, thallium and silver. More preferred is X-type or Y-type zeolite having at least one cation selected from lithium, sodium, magnesium, calcium, strontium, lead, thallium and silver. As the cation, especially preferred are lithium, sodium, magnesium, calcium, strontium, lead and silver. As the desorbent, concretely, preferred are chlorotoluene and chlorobenzene, and more preferred is o-chlorotoluene.

In the invention where an o-halogeno-n-alkylbenzene is separated as the extract component, preferably used is X-type or Y-type zeolite having at least one cation selected from alkali metals, alkaline earth metals, lead, thallium and silver. More preferred is X-type or Y-type zeolite having at least one cation selected from sodium, potassium, rubidium, cesium, magnesium, calcium, strontium, lead, thallium and silver. As the cation, especially preferred are sodium, potassium, rubidium, calcium, strontium and silver. As the desorbent, concretely, preferred are chlorotoluene and chlorobenzene, and more preferred are p-chlorotoluene, m-chlorotoluene and chlorobenzene.

In the invention where a p-halogeno-sec-alkylbenzene is separated as the extract component, preferably used is X-type or Y-type zeolite having at least one cation selected from alkali metals, alkaline earth metals, lead, thallium and silver. More preferred is X-type or Y-type zeolite having at least one cation selected from potassium, rubidium and barium. As the cation, especially preferred are potassium and barium. As the desorbent, concretely, preferred are chlorotoluene and chlorobenzene, and more preferred are o-chlorotoluene, m-chlorotoluene and chlorobenzene.

In the invention where an m-halogeno-sec-alkylbenzene is separated as the extract component, preferably used is X-type or Y-type zeolite having at least one cation selected from alkali metals, alkaline earth metals, lead, thallium and silver. More preferred is X-type or Y-type zeolite having at least one cation selected from lithium, sodium, rubidium, potassium, cesium, magnesium, barium and thallium. As the cation, especially preferred are lithium, potassium, rubidium, cesium, magnesium, barium and thallium. As the desorbent, concretely, preferred are chlorotoluene, chlorobenzene and xylene, and more preferred are p-chlorotoluene, m-chlorotoluene, o-chlorotoluene and chlorobenzene.

In the invention where a p-halogeno-sec-alkylbenzene is separated as the raffinate component, preferably used is X-type or Y-type zeolite having at least one cation selected from alkali metals, alkaline earth metals, lead, thallium and silver. More preferred is X-type or Y-type zeolite having at least one cation selected from lithium, sodium, potassium, cesium, rubidium, magnesium, calcium, strontium, thallium and silver. AS the cation, especially preferred are lithium, sodium, cesium, magnesium, calcium, strontium, thallium and silver. As the desorbent, concretely, preferred are chlorotoluene and chlorobenzene, and more preferred are p-chlorotoluene, m-chlorotoluene and chlorobenzene.

In the invention where an o-halogeno-sec-alkylbenzene is separated as the raffinate component, preferably used is pentacyl-type zeolite having an alkali metal cation, or X-type or Y-type zeolite having at least one cation selected from alkali metals, alkaline earth metals, thallium, and silver. More preferred is pentacyl-type zeolite having at least one cation selected from lithium and sodium, or X-type or Y-type zeolite having at least one cation selected from lithium, sodium, potassium, rubidium, cesium, magnesium, calcium, strontium, thallium and barium. As the cation, especially preferred are lithium, sodium, potassium, rubidium, cesium, magnesium, strontium, thallium and barium. As the desorbent, concretely, preferred are chlorotoluene and chlorobenzene, and more preferred are m-chlorotoluene and o-chlorotoluene.

In the invention where an o-halogeno-n-alkylbenzene is separated as the raffinate component, preferably used is X-type or Y-type zeolite having at least one cation selected from alkali metals, alkaline earth metals, lead, thallium and silver. More preferred is X-type or Y-type zeolite having at least one cation selected from lithium, cesium, magnesium, barium and thallium. As the cation, especially preferred are lithium, cesium, magnesium and barium. As the desorbent, concretely, preferred are chlorotoluene and chlorobenzene, and more preferred is o-chlorotoluene.

In the invention where an m-halogeno-n-alkylbenzene is separated as the raffinate component, preferably used is Y-type zeolite having at least one cation selected from alkali metals, lead, thallium and silver, more preferably from lead, potassium, cesium and rubidium. As the cation, especially preferred are potassium, cesium and lead. As the desorbent, concretely, preferred are chlorotoluene, chlorobenzene and xylene, and more preferred is at least one selected from o-chlorotoluene, o-xylene and m-xylene.

In the invention where p-halogeno-n-alkylbenzene is separated as the raffinate component, preferably used is X-type or Y-type zeolite having at least one cation selected from alkali metals, alkaline earth metals, thallium and silver. More preferred is X-type or Y-type zeolite having at least one cation selected from lithium, sodium, potassium, rubidium, cesium, magnesium, calcium, barium, thallium and silver. As the cation, especially preferred are lithium, potassium, cesium, magnesium, calcium, barium, thallium and silver. As the desorbent, concretely, preferred are chlorotoluene, chlorobenzene and xylene, and more preferred are m-chlorotoluene, o-chlorotoluene and chlorobenzene.

As a rule, the adsorbing capabilities of adsorbents may be indicated by adsorption selectivity ($\alpha$) of the following formula:

$$\alpha_{A/B} = \text{(weight fraction of component A/weight fraction of component B)}_s / \text{(weight fraction of component A/weight fraction of component B)}_L$$

wherein
- A and B each indicate any one isomer of an aromatic compound;
- S indicates an adsorbed phase; and
- L indicates a liquid phase as equilibrated with the adsorbed phase.

Where the value of the above formula is larger than 1, the component A is selectively adsorbed by the adsorbent; and where the value is smaller than 1, the component B is selectively adsorbed by it. Adsorbents having a value α of the formula of larger than 1 (or those having it smaller than 1 and nearer to 0) are more effective for adsorptive separation of A and B from each other.

As described above, efficient adsorptive separation of a specific isomer from a mixture of isomers of an aromatic compound having an alkyl group with at least 3 carbon atoms is possible according to the invention.

Aromatic compounds having an alkyl group with at least 3 carbon atoms can be produced efficiently in the invention, in which, preferably, the steps noted above are combined. More preferably, at least one of the steps (1), (2) and (3) mentioned below is followed by the step (4).

(1) A step of contacting a starting material that contains an aromatic compound having a branched alkyl group with at least 3 carbon atoms, with a zeolite-containing catalyst in a liquid phase in the presence of hydrogen therein, thereby changing the position of the carbon atoms of the alkyl group bonding to the aromatic ring of the compound.

(2) A step of contacting a starting material that contains an aromatic compound having a branched alkyl group with at least 3 carbon atoms, with a catalyst containing zeolite and containing rhenium and/or silver, thereby changing the position of the carbon atoms of the alkyl group bonding to the aromatic ring of the compound.

(3) A step of contacting a halogenated aromatic compound having an alkyl group with at least 3 carbon atoms, with an acid-type catalyst, thereby isomerizing the compound.

(4) A step of treating a mixture of isomers of an aromatic compound having an alkyl group with at least 3 carbon atoms, with a zeolite adsorbent that contains at least one exchanging cation selected from alkali metals, alkaline earth metals, lead, thallium and silver, thereby separating a specific isomer from the isomer mixture through adsorption.

The aromatic compounds having an alkyl group with at least 3 carbon atoms, which are produced according to the invention, can be converted into their derivatives, through oxidation or halogenation at the alkyl group of the compounds.

The derivatives of the aromatic compounds having an alkyl group with at least 3 carbon atoms, which are produced according to the invention followed by oxidation, include, for example, aromatic ketones and aromatic alcohols. Specific examples of the compounds are propiophenone, butyrophenone, valerophenone, o-chloropropiophenone, m-chloropropiophenone, p-chloropropiophenone, o-chlorobutyrophenone, m-chlorobutyrophenone, p-chlorobutyrophenone, o-chlorovalerophenone, m-chlorovalerophenone, p-chlorovalerophenone, 1-phenylpropanol, 1-phenylbutanol, 1-phenylpentanol, 1-(2'-chlorophenyl)propanol, 1-(3'-chlorophenyl)propanol, 1-(4'-chlorophenyl)propanol, 1-(2'-chlorophenyl)butanol, 1-(3'-chlorophenyl)butanol, 1-(4'-chlorophenyl)butanol, 1-(2'-chlorophenyl)pentanol, 1-(2'-chlorophenyl)pentanol, 1-(4'-chlorophenyl)pentanol, o-bromopropiophenone, m-bromopropiophenone, p-bromopropiophenone, o-bromobutyrophenone, m-bromobutyrophenone, p-bromobutyrophenone, o-bromovalerophenone, m-bromovalerophenone, p-bromovalerophenone, 1-phenylpropanol, 1-phenylbutanol, 1-phenylpentanol, 1-(2'-bromophenyl)propanol, 1-(3'-bromophenyl)propanol, 1-(4'-bromophenyl)propanol, 1-(2'-bromophenyl)butanol, 1-(3'-bromophenyl)butanol, 1-(4'-bromophenyl)butanol, 1-(2'-bromophenyl)pentancl, 1-(3'-bromophenyl)pentanol, 1-(4'-bromophenyl)pentanol, 2-phenyl-2-propanol, and 2-phenyl-2-butanol.

For oxidizing the aromatic compounds, for example, employable is liquid-phase oxidation using, as the oxidizing agent, any of molecular oxygen, hydrogen peroxide, peracetic acid, tert-butyl peroxide, perbenzoic acid, or sodium hypochlorite; or vapor-phase oxidation using molecular oxygen as the oxidizing agent.

The derivatives of the aromatic compounds having an alkyl group with at least 3 carbon atoms, which are produced according to the invention followed by halogenation at the alkyl group, may be any of monohalides, dihalides, trihalides and tetrahalides. Specific examples of the derivatives are 1-chloro-1-phenylpropane, 1-chloro-2-phenylpropane, 2-chloro-1phenylpropane, 2-chloro-2-phenylpropane, 1-chloro-3-phenylpropane, 1-chloro-1-phenylbutane, 1-chloro-2-phenylbutane, 2-chloro-1-phenylbutane, 2-chloro-2-phenylbutane, 2-chloro-3-phenylbutane, 2-4-phenylbutane, 1-chloro-4-phenylbutane, 1-chloro-1-phenylpentane, 1-chloro-2-phenylpentane, 2-chloro-1-phenylpentane, 2-chloro-2-phenylpentane, 3-chloro-1-phenylpentane, 3-chloro-2-phenylpentane, 2-chloro-5-phenylpentane, 1-chloro-1-chlorophenylpropane, 1-chloro-2-chlorophenylpropane, 2-chloro-1-chlorophenylpropane, 2-chloro-2-chlorophenylpropane, 1-chloro-3-chlorophenylpropane, 1-chloro-1-chlorophenylbutane, 1-chloro-2-chlorophenylbutane, 2-chloro-1-chlorophenylbutane, 2-chloro-2-chlorophenylbutane, 2-chloro-3-chlorophenylbutane, 2-chloro-4-chlorophenylbutane, 1-chloro-4-chlorophenylbutane, 1-chloro-1-chlorophenylpentane, 1-chloro-2-chlorophenylpentane, 2-chloro-1-chlorophenylpentane, 2-chloro-2-chlorophenylpentane, 3-chloro-1-chlorophenylpentane, 3-chloro-2-chlorophenylpentane, 2-chloro-5-chlorophenylpentane, 1-chloro-1-bromophenylpropane, 1-chloro-2-bromophenylpropane, 2-chloro-1-bromophenylpropane, 2-chloro-2-bromophenylpropane, 1-chloro-3-bromophenylpropane, 1-chloro-1-bromophenylbutane, 1-chloro-2-bromophenylbutane, 2-chloro-1-bromophenylbutane, 2-chloro-2-bromophenylbutane, 2-chloro-3-bromophenylbutane, 2-chloro-4-bromophenylbutane, 1-chloro-4-bromophenylbutane, 1-chloro-1-bromophenylpentane, 1-chloro-2-bromophenylpentane, 2-chloro-1-bromophenylpentane, 2-chloro-2-bromophenylpentane, 3-chloro-1-bromophenylpentane, 3-chloro-2-bromophenylpentane, 2-chloro-5-bromophenylpentane, 1-bromo-1-chlorophenylpentane, 1-bromo-2-chlorophenylpropane, 2-bromo-1-chlorophenylpropane, 2-bromo-2-chlorophenylpropane, 1-bromo-3-chlorophenylpropane, 1-bromo-1-chlorophenylbutane, 1-bromo-2-chlorophenylbutane, 2-bromo-1-chlorophenylbutane, 2-bromo-2-chlorophenylbutane, 2-bromo-2-chlorophenylbutane, 2-bromo-4-chlorophenylbutane, 1-bromo-4-chlorophenylbutane, 1-bromo-1-chlorophenylbutane, 1-bromo-2-chlorophenylpentane, 2-bromo-1- chlorophenylpentane, 2-bromo-2-chlorophenylpentane, 3-bromo-2-chlorophenylpentane, 3-bromo-2-chlorophenylpentane, and 2-bromo-5-chlorophenylpentane.

For halogenating the aromatic compounds having an alkyl group with at least 3 carbon atoms, for example, employable is a method of halogenating them with a halogenating agent of, for example, chlorine or bromine, in the presence of a radical initiator or with the compounds being exposed to light. The radical initiator is not specifically defined, but preferred is benzoyl peroxide or 2,2'-azobisisobutyronitrile.

The invention is described in more detail with reference to the following Examples, which, however, are not intended to restrict the scope of the invention.

Conversion of aromatic compounds for changing the position of carbon atoms of the alkyl group bonding to aromatic ring of the compounds:

As aromatic compounds having a branched alkyl group with at least 3 carbon atoms, used were a special-grade chemical, isopropylbenzene (from Wako Pure Chemicals) and a special-grade chemical, sec-butylbenzene (from Tokyo Chemical). An isomer mixture of chloroisopropylbenzene was prepared by chlorinating isopropylbenzene at its benzene ring followed by purifying the resulting chloride through distillation, in the manner mentioned below. As additional aromatic compounds to be in the reaction system, used were a special-grade chemical, benzene (from Nacalai Tesque) and a special-grade chemical, chlorobenzene (from Katayama Chemical).

Preparation of isomer mixture of chloroisopropylbenzene:

120 g of isopropylbenzene, and 6 g of powder of L-type zeolite (from Tosoh, calcined at 600° C.) were put into a 200 ml three-neck flask (equipped with condenser, gas intake duct and thermometer). While stirred with a magnetic stirrer, this was purged with nitrogen, and chlorine was introduced thereinto for 11 hours, at a flow rate of 3600 ml/hr and at a controlled reaction temperature of 40° C. The conversion of isopropylbenzene was 99%. The reaction mixture was washed with water for dehydrochlorination, and then subjected to distillation under reduced pressure (at 100° C., 0.0065 MPa) to obtain a mixture of chloroisopropylbenzene isomers (o-isomer/m-isomer/p-isomer=16/1/83).

Preparation of catalysts:

Catalyst 1:

To powder of MFI-type zeolite ($SiO_2/Al_2O_3$=25.2 mol/mol) that had been prepared according to the method of Example 1 in Japanese Patent Laid-Open No. 189719/1981, added was alumina sol in an amount of 15% by weight in terms of $Al_2O_3$, mixed and kneaded, then shaped through extrusion into 14 to 24-mesh pellets, and calcined in air at 500° C. for 2 hours. The zeolite pellets were ion-exchanged five times in an aqueous solution of 10 wt. % ammonium chloride (liquid/solid ratio, 2.0 cc/g) at 90° C., then well washed with water, dried at 120° C. for 15 hours, and thereafter calcined in air at 550° C. for 2 to obtain an acid-type zeolite catalyst.

Catalyst 2:

To power of MFI-type zeolite ($SiO_2/Al_2O_3$=25.2 mol/mol) that had been prepared according to the method of Example 1 in Japanese Patent Laid-Open No. 189719/1981, added was alumina sol in amount of 15% by weight in terms of $Al_2O_3$, mixed and kneaded, then shaped through extrusion into 14 to 24-mesh pellets, and calcined in air at 500° C. for 2 hours. The zeolite pellets were ion-exchanged five times in an aqueous solution of 10 wt. % ammonium chloride (liquid/solid ratio, 2.0 cc/g) at 90° C., then well washed with water, and dried at 120° C. for 15 hours. To 20 g of the thus-processed zeolite, added was 6.5 g of an aqueous solution of 2 wt. % $Re_2O_7$. To this, further added was distilled water to be in a liquid/solid ratio of 1.4 cc/g. This was left at room temperature for 4 hours, while being stirred every one hour, and filtered. The resulting residue was dried at 120° C. for 15 hours and then calcined in air at 550° C. for 2 hours to obtain an Re-containing, acid-type zeolite catalyst.

Catalyst 3:

To powder of MFI-type zeolite ($SiO_2/Al_2O_3$=25.2 mol/mol) that had been prepared according to the method of Example 1 in Japanese Patent Laid-Open No. 189719/1981, added was 25 part of SCF alumina (from Condea). To this, further added was alumina sol in an amount of 15% by weight in terms of $Al_2O_3$, mixed and kneaded, then shaped through extrusion into 14 to 24-mesh pellets, and calcined in air at 500° C. for 2 hours. The zeolite pellets were ion-exchanged five times in an aqueous solution of 10 wt. % ammonium chloride (liquid/solid ratio, 2.0 cc/g) at 90° C., then well washed with water, and dried at 120° C. for 15 hours. To 20 g of the thus-processed zeolite, added was 6.5 g of an aqueous solution of 2 wt. % $Re_2O_7$. To this, further added was distilled water to be in a liquid/solid ratio of 1.4 cc/g. This was left at room temperature for 4 hours, while being stirred every one hour, and filtered. The resulting residue was dried at 120° C. for 15 hours and then calcined in air at 550° C. for 2 hours to obtain an Re-containing, acid-type zeolite catalyst.

Catalyst 4:

To powder of MFI-type zeolite ($SiO_2/Al_2O_3$=25.2 mol/mol) that had been prepared according to the method of Example 1 in Japanese Patent Laid-Open No. 189719/1981, added was 25 parts of SCF alumina (from Condea). To this, further added was alumina sol in an amount of 15% by weight in terms of $Al_2O_3$, mixed and kneaded, then shaped through extrusion into 14 to 24-mesh pellets, and calcined in air at 500° C. for 2 hours. The zeolite pellets were ion-exchanged five times in an aqueous solution of 10 wt. % ammonium chloride (liquid/solid ratio, 2.0 cc/g) at 90° C., then well washed with water, and dried at 120° C. for 15 hours. To 20 g of the thus-processed zeolite, added was 6.5 g of an aqueous solution of 2 wt. % $Re_2O_7$. To this, further added was distilled water to be in a liquid/solid ratio of 1.4 cc/g. This was left at room temperature for 4 hours, while being stirred every one hour, and filtered. The resulting residue was dried at 120° C. for 15 hours, and then packed into a glass tube having an inner diameter of 40 mm. With a hydrogen sulfide stream (purity 100%, $H_2S$ flow rate 5 cc/min) being introduced into the tube, this was heated at 250° C. under atmospheric pressure for 2 hours. Next, this was calcined in air at 550° C. for 2 hours to obtain an Re-containing, acid-type zeolite catalyst.

Catalyst 5:

To powder of MFI-type zeolite ($SiO_2/Al_2O_3$=25.2 mol/mol) that had been prepared according to the method of Example 1 in Japanese Patent Laid-Open No. 189719/1981, added was 300 parts of SCF alumina (from Condea). To this, further added was alumina sol in an amount of 15% by weight in terms of $Al_2O_3$, mixed and kneaded, then shaped through extrusion into 14 to 24-mesh pellets, and calcined in air at 500° C. for 2 hours. The zeolite pellets were ion-exchanged five times in an aqueous solution of 10 wt. % ammonium chloride (liquid/solid ratio, 2.0 cc/g) at 90° C., then well washed with water, and dried at 120° C. for 15 hours. 20 g of the thus-processed zeolite was packed into a quartz tube having an inner diameter of 40 mm. With an air stream (flow rate, 4.3 liters/hr, having a water vapor pressure of 0.194 MPa at 60° C.) being introduced into the tube, this was processed with steam at 550° C. for 6 hours. To the thus-processed zeolite, added was 6.5 g of an aqueous solution of 2 wt.% $Re_2O_7$. To this, further added was distilled water to be in a liquid/solid ratio of 1.4 cc/g. This was left at room temperature for 4 hours, while being stirred every one hour, and filtered. The resulting residue was dried at 120° C. for 15 hours, and then packed into a glass tube having an inner diameter of 40 mm. With a hydrogen sulfide stream (purity 100%, $H_2S$ flow rate 5 cc/min) being introduced into the tube, this was heated at 250° C. under atmospheric pressure for 2 hours. Next, this was calcined in air at 550° C. for 2 hours to obtain an Re-containing, acid-type zeolite catalyst.

EXAMPLE 1

7 g of catalyst 1 that had been prepared as above was set in a fixed-bed flow reaction system, to which was applied a feed comprised of isopropylbenzene and benzene along with hydrogen. In that condition, the material was contacted with the catalyst. The reaction condition is shown below.

Feed composition:
 benzene/isopropylbenzene=4/1 (mol/mol)
 WHSV (flow rate of feed/amount of catalyst)=3.0 $hr^{-1}$
Hydrogen supply:
 hydrogen/feed=0.03/1 (mol/mol)
Reaction temperature: 250° C.
Reaction pressure: 5 MPa After the reaction, the resulting liquid was analyzed through gas chromotography, and the yield of n-propylbenzene was obtained according to the following formula:

Yield of n-propylbenzene (%) =(mols of n-propylbenzene in the reaction mixture)/(mols of isopropylbenzene in the feed)×100

The data are plotted in FIG. 1. the deactivation rate of the catalyst used was −1.0%/day.

EXAMPLE 2

The same process as in Example 1 was repeated, except that catalyst 2 was used herein.

The data are plotted in FIG. 1. The deactivation rate of the catalyst used was −0.3%/day.

COMPARATIVE EXAMPLE 1

The same process as in Example 1 was repeated, except that no hydrogen was supplied to the reaction system herein.

The data are plotted in FIG. 1. The deactivation rate of the catalyst used was −1.3%/day.

EXAMPLE 3

10 g of catalyst 2 that had been prepared as above was set in a fixed-bed flow reaction system, to which was applied a feed comprised of an isomer mixture of chloroisopropylbenzene and chlorobenzene along with hydrogen. In that condition, the feed was contacted with the catalyst. The reaction condition is shown below.

Feed composition:
 chlorobenzene/chloroisopropylbenzene isomers=4/1 (mol/mol)
 WHSV (flow rate of feed/amount of catalyst)=2.0 $hr^{-1}$
Hydrogen supply:
 hydrogen/feed=0.06/1 (mol/mol)
Reaction temperature: 240° C.
Reaction pressure: 5 MPa After the reaction, the resulting liquid was analyzed through gas chromatography, and the yield of m-chloro-n-propylbenzene was obtained according to the following formula:

Yield of m-chloro-n-propylbenzene (%) =(mols of m-chloro-n-propylbenzene in the reaction mixture)/(mols of chloroisopropylbenzene in the feed)×100

Figure 2:
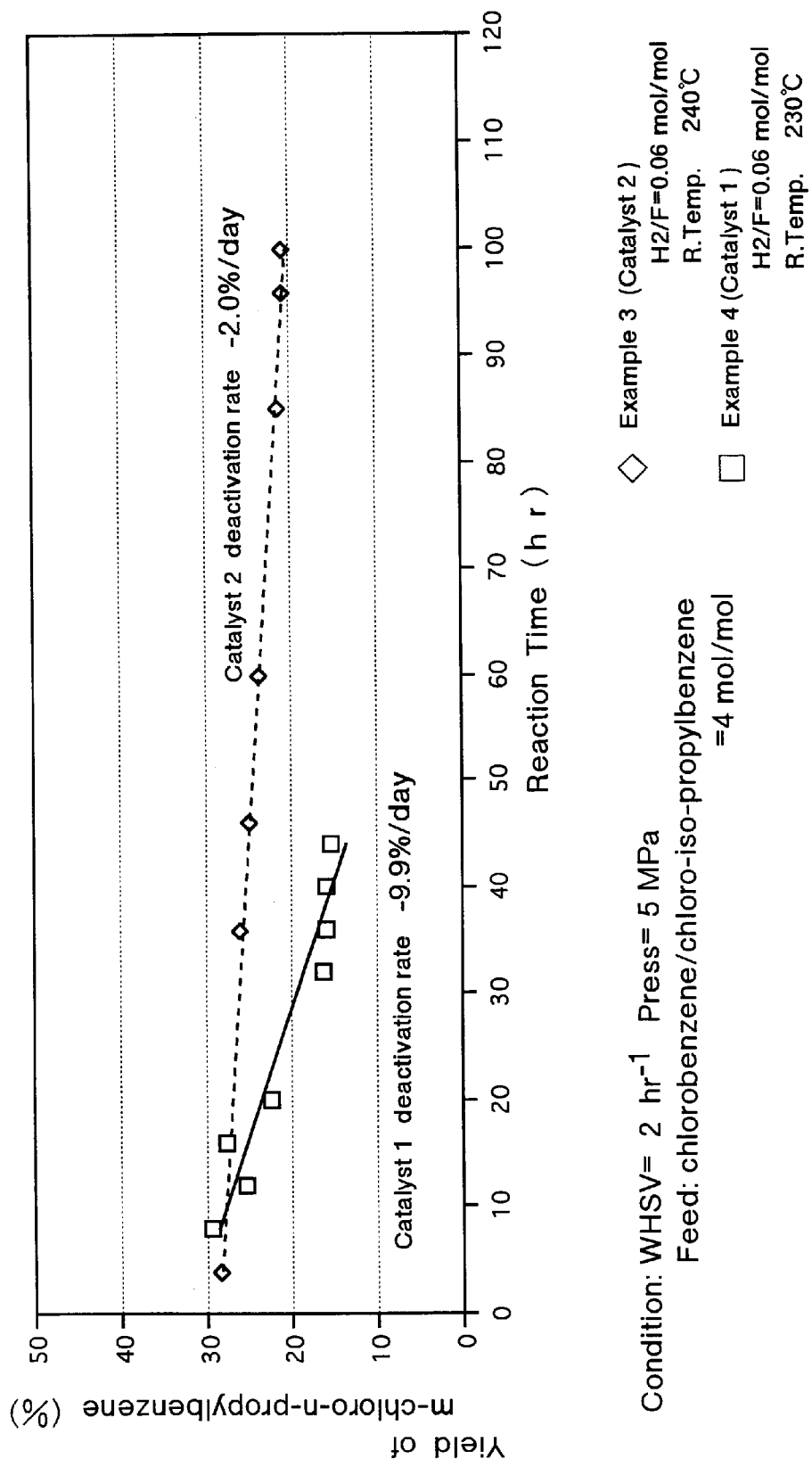
FIG. 2 is a graph showing the yield of m-chloro-n-propylbenzene versus reaction time in Examples 3 and 4.

The data are plotted in FIG. 2. The deactivation rate of the catalyst used was −2.0%/day.

EXAMPLE 4

The same process as in Example 3 was repeated, except that 10 g of catalyst 1 that had been prepared as above was used and the reaction temperature was 230° C. herein.

The data are plotted in FIG. 2. The deactivation rate of the catalyst used was −9.9%/day.

EXAMPLE 5

The same process as in Example 3 was repeated, except that 10 g of catalyst 3 that had been prepared as above was used and the reaction temperature was 250° C. herein.

Figure 3:
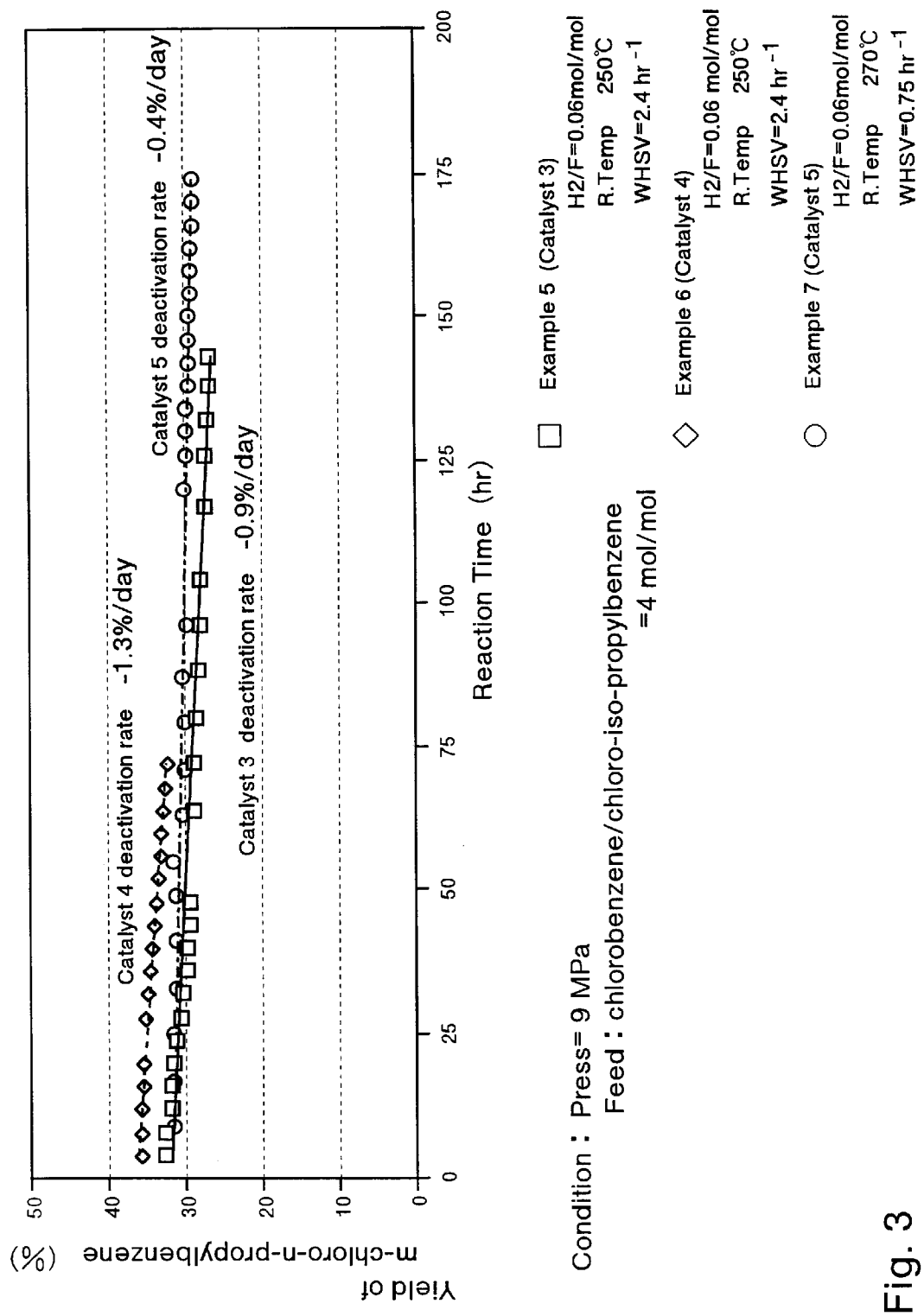
FIG. 3 is a graph showing the yield of m-chloro-n-propylbenzene versus reaction time in Examples 5, 6 and 7.

The data are plotted in FIG. 3. The deactivation rate of the catalyst used was −0.9%/day.

EXAMPLE 6

The same process as in Example 5 was repeated, except that 10 g of catalyst 4 that had been prepared as above was used herein.

The data are plotted in FIG. 3. The deactivation rate of the catalyst used was −1.3%/day.

EXAMPLE 7

The same process as in Example 5 was repeated, except that 10 g of catalyst 5 that had been prepared as above was used and the reaction temperature was 270° C. herein.

The data are plotted in FIG. 3. The deactivation rate of the catalyst used was −0.4%/day.

EXAMPLE 8

7 g of catalyst 3 that had been prepared as above was set in a fixed-bed flow reaction system, to which was applied feed comprised of sec-butylbenzene and benzene along with hydrogen. In that condition, the material was contacted with the catalyst. The reaction condition is shown below.

Feed composition:
 benzene/sec-butylbenzene=4/1 (mol/mol)
 WHSV (flow rate of feed/amount of catalyst)=2.3 $hr^{-1}$
Hydrogen supply:
 hydrogen/feed=0.04/1 (mol/mol)
Reaction temperature: 250° C.
Reaction pressure: 9 MPa After the reaction, the resulting liquid was analyzed through gas chromatography, and the yield of n-butylbenzene was obtained according to the following formula:

Yield of n-butylbenzene (%) =(mols of n-butylbenzene in the reaction mixture)/(mols of sec-butybenzene in the feed)×100

Figure 4:
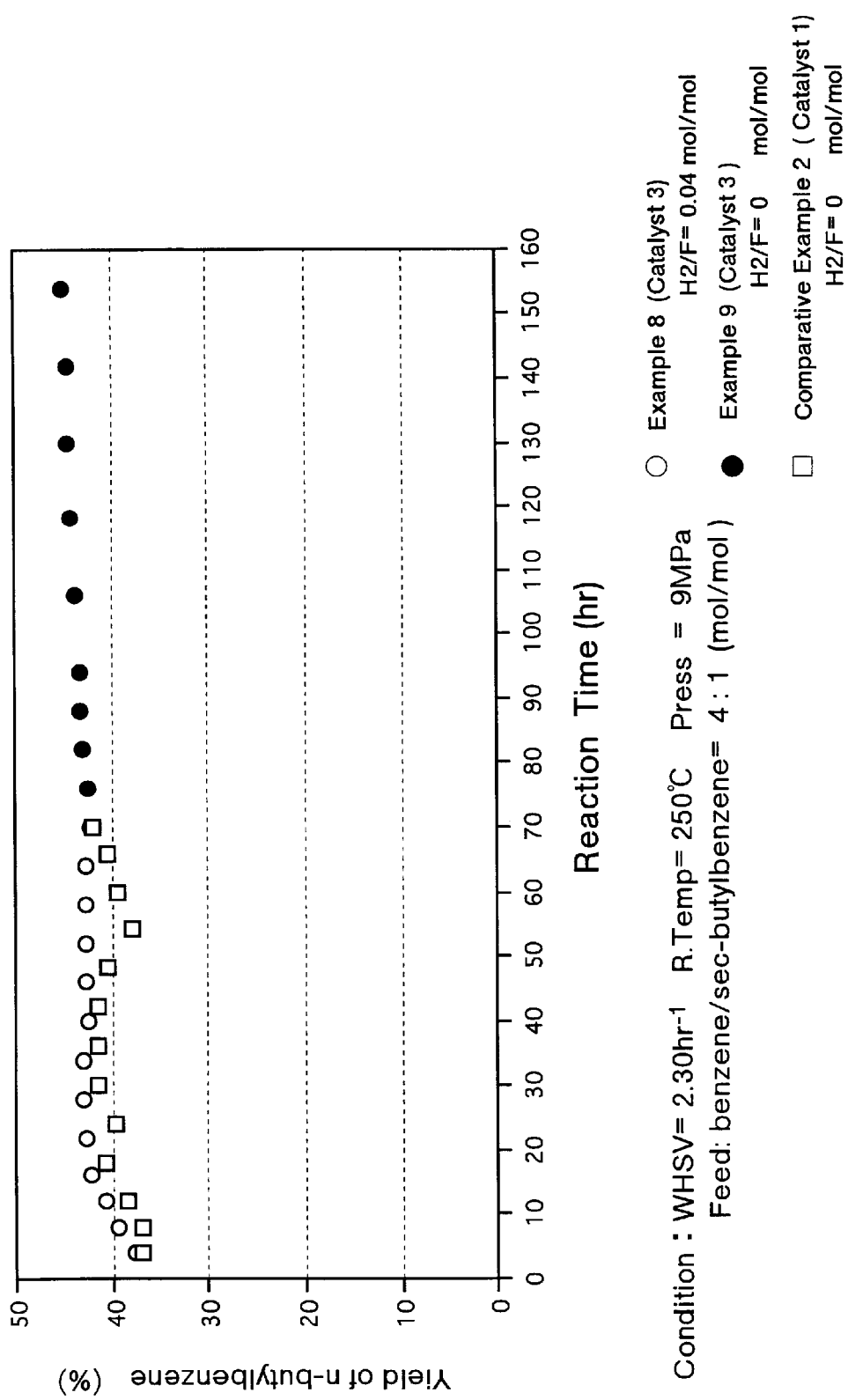
FIG. 4 is a graph showing the yield of n-butylbenzene versus reaction time in Examples 8 and 9 and Comparative Example 2.

The data are plotted in FIG. 4. The catalyst used was deactivated little.

In addition to the product of n-butylbenzene, the reaction mixture contained other products of isobutylbenzene and tert-butylbenzene. After the reaction time of 64 hours, the ratio of the isomers in the reaction mixture was as follows:

sec-butyl/n-butyl/isobutyl/tert-butylbenzene =34.3/42.8/21.8/1.1

EXAMPLE 9

In the process of Example 8, the hydrogen supply was stopped after 64 hours, and the reaction was continued further.

The data are plotted in FIG. 4. The catalyst used was deactivated little.

COMPARATIVE EXAMPLE 2

The same process as in Example 8 was repeated, except that 7 g of catalyst 1 that had been prepared as above was used and no hydrogen was applied to the reaction system herein.

The data are plotted in FIG. 4. The catalyst used was deactivated little, but its activity was lower than the activity of the catalyst in Example 8.

Isomerization of halogenated aromatic compound having alkyl group with at least 3 carbon atoms:

In the following Examples, used were Y-type zeolite (US-Y:CBV712 from PQ, $SiO_2/Al_2O_3$=11.5), beta-type zeolite (CP811BL from PQ, $SiO_2/Al_2O_3$=22.9), mordenite-type zeolite ($SiO_2/Al_2O_3$=19.5) that had been prepared according to the method of Example 1 in Japanese Patent Laid-Open No. 31006/1990, and pentacyl-type zeolite ($SiO_2/Al_2O_3$=20) that had been prepared according to the method of Example 1 in Japanese Patent Laid-Open No. 189719/1981.

As the source of a metal of Groups 7 to 11, an aqueous solution of 2 wt.% $Re_2O_7$ (from Kisan Metal) was used in the following Examples.

Preparation of isomer mixture of chloroisoproylbenzene:

120 g of a special-grade chemical, isopropylbenzene (from Tokyo Chemical), and 6 g of powder of L-type zeolite (from Tosoh, calcined at 600° C.) were put into a 200 ml three-neck flask (equipped with condenser, gas intake duct and thermometer). While stirred with a magnetic stirrer, this was purged with nitrogen, and chlorine was introduced thereinto for 11 hours, at a flow rate of 3600 ml/hr and at a controlled reaction temperature of 40° C. The conversion of isopropylbenzene was 99%. The reaction mixture was washed with water for dehydrochloroination, and then subjected to distillation under reduced pressure (at 100° C., 50 mmHg) to obtain a mixture of chloroisopropylbenzene isomers (o-isomer/m-isomer/p-isomer=16/1/83) (feed 1).

Preparation of m-chloropropylbenzene:

M-chloropropiophenone (from Aldrich) was reduced with hydrazine hydrate (through Wolff-Kishner reduction) to obtain m-chloropropylbenzene.

Precisely, 980 g (5.8 mols) of a special-grade chemical, m-chloropropiophenone (from Avocado), 1.1 kg of a special-grade chemical, diethylene glycol (from Katayama Chemical), 600 g (10.7 mols) of potassium hydroxide (from Katayama Chemical), and 600 g (9.6 mols) of 80% hydrazine hydrate (from Katayama Chemical) were put into a 10 liters separable flask equipped with an air-cooling fractionation tower, a mechanical stirrer and a thermometer, and the temperature of the mantle heater around the flask was elevated up to 120° C. with the mixture in the flask being stirred. After the temperature of the vapor (this is a hydrazone product) flowing out of the flask was stabilized, the temperature in the flask was further elevated until the temperature of the flowing vapor reached 110° C., at which the mixture in the flask was reacted for about 8 hours.

The absence of the hydrazone product in the reaction mixture was confirmed through GC analysis, and the reaction mixture was left cooled with water applied thereto. Then, m-chlorobenzene was extracted out of the mixture with hexane, again washed with water, and purified through distillation under reduced pressure (feed 3).

Preparation of p-chloropropylbenzene:

In the same manner as previously for preparing m-chloropropylbenzene from m-chloropropiophenone (from Aldrich), p-chloropropylbenzene was prepared from p-chloropropiophenone (from Aldrich) (feed 2).

Preparation of o-chloropropylbenzene:

480 g of a special-grade chemical, propylbenzene (from Tokyo Chemical) and 12 g of ferric chloride (from Wako Pure Chemicals) were put into a 1000 ml three-neck flask (equipped with condenser, gas intake duct and thermometer). While stirred with a magnetic stirrer, this was purged with nitrogen, and chlorine gas was introduced thereinto for 11 hours, at a flow rate of 4200 ml/hr and at a controlled reaction temperature of about 50° C. The conversion of propylbenzene was about 97%. A large amount of water was added to the reaction mixture to thereby decompose ferric chloride, and the aqueous phase was removed. Then, the mixture was subjected to distillation under reduced pressure (at 85° C., 20 mmHg) to obtain o-chloropropylbenzene (o-isomer/m-isomer/p-isomer=71/4/25) (feed 4).

Preparation of catalysts:

Catalyst 6:

15 parts by weight, in terms of alumina, of alumina sol ($Al_2O_3$ content=10 wt. %) was added to 100 parts by weight of the Y-type zeolite noted above, shaped, then dried overnight at 120° C., and thereafter calcined at 500° C. for 2 hours.

Catalyst 7:

15 parts by weight, in terms of alumina, of alumina sol ($Al_2O_3$ content=10 wt. %) was added to 100 parts by weight of the beta-type zeolite noted above, shaped, then dried overnight at 120° C., and thereafter calcined at 500° C. for 2 hours. The thus-shaped zeolite was ion-exchanged five times in an aqueous solution of 10 wt. % ammonium chloride (liquid/solid ratio, 2.0 cc/g) at 90° C. for 1 hour, then well washed with distilled water, dried overnight at 120° C., and thereafter calcined in air at 550° C. for 2 hours to obtain an acid-type, beta-type zeolite catalyst.

Catalyst 8:

Mordenite-type zeolite was shaped in the same manner as for catalyst 7. This was ion-exchanged once in an aqueous solution of 10 wt. % ammonium chloride (liquid/solid ratio, 2.0 liters/kg) at 85° C. for 1 hour, then well washed with distilled water, dried overnight at 120° C., and thereafter calcined in air at 520° C. for 2 hours to obtain an acid-type, mordenite-type zeolite catalyst.

Isomerization:

EXAMPLE 10

Catalyst 6 (1.5 g) and a mixture of chlorobenzene/chloroisopropylbenzene isomer mixture (feed 1) =4 mol/mol (6 g) were put into a 12 ml autoclave, heated in a thermostat at a reaction temperature of 250° C. for 4 hours, and then cooled. The reaction mixture was analyzed through gas chromatography. The data are in Table 1.

EXAMPLE 11

The same process as in Example 10 was repeated, except that catalyst 8 was used in place of catalyst 6 and the reaction temperature was 230° C. herein. The data are in Table 1.

TABLE 1

|  | feed 1 | Example 10 | Example 11 |
|---|---|---|---|
| Catalyst |  | Catalyst 6 | Catalyst 8 |
| feed/Catalyst (g/g) |  | 4 | 4 |
| Temperature (° C.) |  | 250 | 230 |
| Time (hr) |  | 4 | 4 |
| feed Composition (%) |  |  |  |
| CB | 75.04 | 76.05 | 76.20 |
| o-ClPB | 4.52 | 3.30 | 3.53 |
| m-ClPB | 0.32 | 13.45 | 13.48 |
| p-ClPB | 20.09 | 5.85 | 5.91 |
| o-CPB |  | 0.06 | 0.08 |
| m-CPB |  | 0.02 | 0.04 |
| p-CPB |  | 0.03 | 0.03 |

TABLE 1-continued

|  | feed 1 | Example 10 | Example 11 |
|---|---|---|---|
| (CPB + ClPB) Recovery (%) |  | 90.65 | 91.94 |

CB: chlorobenzene
ClPB: chloroisopropylbenzene
CPB: Chloro-n-propylbenzene

EXAMPLE 12

Catalyst 7 (0.3 g) and p-chloro-n-propylbenzene (feed 2; 3 g) were put into a 12 ml autoclave, heated in a thermostat at a reaction temperature of 250° C. for 3 hours, and then cooled. The reaction mixture was analyzed through gas chromatography. The data are in Table 2.

EXAMPLE 13

The same process as in Example 12 was repeated, except that catalyst 8 was used herein in place of catalyst 7. The data are in Table 2.

EXAMPLE 14

The same process as in Example 12 was repeated, except that m-chloro-n-propylbenzene (feed3) was used herein in place of p-chloro-n-propylbenzene. The data are in Table 2.

EXAMPLE 15

The same process as in Example 14 was repeated, except that catalyst 8 was used herein in place of catalyst 7. The data are in Table 2.

EXAMPLE 16

The same process as in Example 15 was repeated, except that o-chloro-n-propylbenzene (feed 4) was used herein in place of m-chloro-n-propylbenzene. The data are in Table 2.

TABLE 2

|  | Feed 2 | Example 12 | Example 13 | Feed 3 | Example 14 | Example 15 | Feed 4 | Example 16 |
|---|---|---|---|---|---|---|---|---|
| Catalyst |  | Catalyst 7 | Catalyst 8 |  | Catalyst 7 | Catalyst 8 |  | Catalyst 8 |
| Feed |  | Feed 2 | Feed 2 |  | Feed 3 | Feed 3 |  | Feed 4 |
| Feed/-Catalyst (g/g) |  | 10 | 3 |  | 10 | 3 |  | 3 |
| Temperature (° C.) |  | 250 | 250 |  | 250 | 250 |  | 250 |
| Time (hr) |  | 3 | 3 |  | 3 | 3 |  | 3 |
| Feed Composition (%) |  |  |  |  |  |  |  |  |
| CB | 0.05 | 7.88 | 1.42 | 0.07 | 4.28 | 0.09 | 0.07 | 2.50 |
| o-ClPB |  | 0.07 | 0.02 |  | 0.04 | 0 |  | 0.05 |
| m-ClPB |  | 0.26 | 0.08 |  | 0.15 | 0.04 |  | 0.17 |
| p-ClPB |  | 0.12 | 0.04 |  | 0.06 | 0.02 |  | 0.07 |
| o-CPB | 0.92 | 5.73 | 1.60 | 0.21 | 11.00 | 2.29 | 70.94 | 62.84 |
| m-CPB | 1.13 | 43.94 | 19.39 | 99.31 | 60.90 | 88.03 | 3.65 | 14.07 |
| p-CPB | 97.73 | 34.40 | 76.33 | 0.04 | 18.82 | 7.60 | 25.34 | 17.21 |
| (ClPB + CPB) Recovery (%) |  | 84.25 | 97.53 |  | 91.12 | 98.35 |  | 94.18 |

CB: chlorobenzene
ClPB: chloroisopropylbenzene
CPB: chloro-n-propylbenzene

From the data as above, it is understood that acid-type zeolite efficiently promotes the isomerization of halogenoisopropylbenzenes or halogeno-n-propylbenzenes contacted with it.

Adsorptive separation:

In the following Examples, the adsorbing capabilities of the adsorbents used for six isomers of chloropropylbenzene, o-chloroisopropylbenzene (oI), m-chloroisopropylbenzene (mI), p-chloroisopropylbenzene (pI), o-chloro-n-propylbenzene (oN), m-chloro-n-propylbenzene (mN) and p-chloro-n-propylbenzene (pN), are indicated by the adsorption selectivity ($\alpha$) of the following formula:

$$\alpha_{A/B} = (\text{weight fraction of component A/weight fraction of component B})_s / (\text{weight fraction of component A/weight fraction of component B})_L$$

wherein

A and B each indicate any one of the chloropropylbenzene isomers;

S indicates an adsorbed phase; and

L indicates a liquid phase as equilibrated with the adsorbed phase.

For representing chloropropylbenzene isomers, used are abbreviations of o, m, p, N and I. Of those, o, m, and p each indicate o-, m- and p-chloropropylbenzenes, respectively; and I and N each indicate chloroisopropylbenzene and chloro-n-propylbenzene, respectively. For example, mN means m-chloro-n-propylbenzene; and pI means p-chloroisopropylbenzene. The component A is mN (m-chloro-n-propylbenzene), in most cases.

Where the value of the above formula is larger than 1, the component A is selectively adsorbed by the adsorbent; and where the value is smaller than 1, the component B is selectively adsorbed by it. Adsorbents having a value α of the formula of large than 1 (or those having it smaller than 1 and nearer to 0) are more effective for adsorptive separation of A and B form each other. For example, in case where the component A is mN, the value α in the formula of larger than 1 means that m-chloro-n-propylbenzene is more easily adsorbed by the adsorbent used than o- ,m- and p-chloroisopropylbenzene and o- and p-chloro-n-propylbenzene, while the value α therein of smaller than 1 means that m-chloro-n-propylbenzene is more hardly adsorbed by the adsorbent used than o- ,m- and p-chloroisopropylbenzene and o- and p-chloro-n-propylbenzene. Accordingly, adsorbents having αmN/oI, αmN/mI, αmN/oN, αmN/pI and αmN/pN of all larger than 1, or all smaller than 1 and nearer to 0 are suitable to separation and recovery of m-chloro-n-propylbenzene. Adsorbents having αmN/mI of smaller than 1 and having the other four α values, αmN/oI, αmN/oN, αmN/pI and αmN/pN of all larger than αmN/mI are suitable to separation and recovery of m-chloroisopropylbenzene as the extract component. Adsorbents having αmN/pI of larger than 1 and having the other four α values, αmN/oI, αmN/mI, αmN/oN and αmN/pN of all smaller than αmN/pI are suitable to separation and recovery of p-chloroisopropylbenzene as the raffinate component.

Preparation of adsorbents:

Table 3 shows various adsorbents used herein. Methods for producing them are mentioned below.

Adsorbent 1: Na—Y

To 100 parts by weight of sodium-type Y-type zeolite (hereinafter referred to as NaY) (powdery product of Zeolum Na-5.1Y, from Tosoh), added was 15 parts by weight, in terms of alumina, of alumina sol (#200 from Nissan Chemical; $Al_2O_3$ content=10 wt. %) serving as a binder, and granulated into granules of from 0.15 to 0.5 mmϕ in size. The granular NaY-type zeolite was dried at 120° C. and then calcined at 500° C.

Adsorbents 2 to 8: M—Y

Adsorbent 1 was ion-exchanged five times in an aqueous solution of 10 wt. % potassium, rubidium, cesium, magnesium, calcium, strontium or barium nitrate (liquid/solid ratio, 4.0 cc/g0 at 80° C. for 30 minutes, then fully washed with distilled water, dried at 120° C. and thereafter calcined at 500° C.

Adsorbent 9: Pb—K—Y

Adsorbent 1 was ion-exchanged ten times in an aqueous solution of 10 wt. % potassium nitrate (from Nacalai Tesque) (liquid/solid ratio, 3.0 cc/g) at 80° C. for 1 hour, and then fully washed with distilled water. Next, this was kept in an aqueous solution of lead nitrate ($Pb(NO_3)_2$, from Nacalai Tesque) (liquid/solid ratio, 3.0 cc/g), of which the lead content corresponds to 40% of the Na cation site in NaY, at room temperature for 30 minutes, and heated therein at 80° C. for 2 hours for ion-exchanging it. Then, this was fully washed with distilled water, dried at 120° C., and calcined at 500° C. for 1 hour.

Adsorbent 10: Cs—Pb–K—Y

Adsorbent 1 was ion-exchanged ten times in an aqueous solution of 10 wt. % potassium nitrate (from Nacalai Tesque) (liquid/solid ratio, 3.0 cc/g) at 80° C. for 1 hour, and then fully washed with distilled water. Next, this was kept in an aqueous solution of lead nitrate ($Pb(NO_3)_2$, from Nacalai Tesque) (liquid/solid ratio, 3.0 cc/g), of which the lead content corresponds to 40% of the Na cation site in NaY, at room temperature for 30 minutes, and heated therein at 80° C. for 2 hours for ion-exchanging it. This was fully washed with distilled water, then kept in an aqueous solution of cesium nitrate ($CsNO_3$, from Kishida Chemical) (liquid/solid ratio, 3.0 cc/g), of which the cesium content corresponds to 20% of the Na cation site in NaY, at room temperature for 30 minutes, and heated therein at 80° C. for 2 hours for ion-exchanging it. Then, this was fully washed with distilled water, dried at 120° C., and calcined at 500° C. for 1 hour.

Adsorbent 11: Na—X

To 100 parts by weight of sodium type X-type zeolite (hereinafter referred to as NaX) powdery product of Zeolum F-9, from Tosoh), added was 20 parts by weight of bentonite

TABLE 3

Adsorbents Used in Examples

| Adsorbent 1 | Adsorbent 2 | Adsorbent 3 | Adsorbent 4 | Adsorbent 5 | Adsorbent 6 | Adsorbent 7 | Adsorbent 8 | Adsorbent 9 |
|---|---|---|---|---|---|---|---|---|
| Na—Y | K—Y | Rb—Y | Cs—Y | Mg—Y | Ca—Y | Sr—Y | Ba—Y | Pb—KY |
| Adsorbent 10 | Adsorbent 11 | Adsorbent 12 | Adsorbent 13 | Adsorbent 14 | Adsorbent 15 | Adsorbent 16 | Adsorbent 17 | Adsorbent 18 |
| Cs—Pb—KY | Na—X | K—X | Rb—X | Cs—X | Mg—X | Ca—X | Sr—X | Ba—X |
| Adsorbent 19 | Adsorbent 20 | Adsorbent 21 | Adsorbent 22 | Adsorbent 23 | Adsorbent 24 | Adsorbent 25 | | |
| 5% Ag—NaX | 10% Cs—NaX | 10% Tl—NaX | 10% Ag—NaX | 10% Li—NaX | 20% Li—NaX | Na—MFI | | | gel (bengel) serving as a binder, and granulated into granules of from 0.15 to 0.3 mmφ in size. The granular NaX-type zeolite was dried at 120° C. and then calcined at 500° C.

Adsorbents 12 to 18: M—X

Adsorbent 11 was ion-exchanged five times in an aqueous solution of 10 wt. %, potassium, rubidium, cesium, magnesium, calcium, strontium or barium nitrate (liquid/solid ratio, 4.0 cc/g) at 80° C. for 30 minutes, then fully washed with distilled water, dried at 120° C. and thereafter calcined at 500° C.

Adsorbents 19 to 24: n%M—NaX

Adsorbent 11 was kept in an aqueous solution of a metal nitrate (metal, M=silver, cerium, thallium, or lithium) (liquid/solid ratio, 3.0 cc/g), of which the metal content corresponds to n % of the Na cation site in Na—X, at room temperature for 30 minutes, and heated therein at 85° C. for 1 hour for ion-exchanging it. Then, this was fully washed with distilled water, dried at 120° C., and calcined at 500° C.

Adsorbent 25: Na-Type pentacyl-type zeolite (Na—MFI)

7.3 g of solid sodium hydroxide (from Katayama Chemical, NaOH content=96.0 wt. %, $H_2O$ content=4.0 wt. %) and 10.2 g of powdery tartaric acid (from Katayama Chemical, tartaric acid content=99.7 wt. %, $H_2O$ content=0.3 wt. %) were dissolved in 583.8 g of water. To the resulting solution, added was 35.4 g of an aqueous solution of sodium aluminate (from Sumitomo Chemical, $Al_2O_3$ content=18.5 wt. %, NaOH content=26.1 wt. %, $H_2O$ content=55.4 wt. %) to prepare a uniform mixture. To the resulting mixture, slowly, added was 111.5 g of powdery silicic acid (Nipseal VN-3 from Nippon Silica, $SiO_2$ content=91.6 wt. %, $Al_2O_3$ content=0.33 wt. %, NaOH content=0.27 wt. %) with stirring to prepare an aqueous slurry mixture. The molar ratios of the components constituting the mixture were as follows:

| | |
|---|---|
| $SiO_2/Al_2O_3$ | 25 |
| $H_2O/SiO_2$ | 20 |
| $OH^-/SiO_2$ | 0.164 |
| $A/Al_2O_3$ | 1.0 |
| | (A: tartrate) |

The mixture was put and sealed in a 1000 ml autoclave, and reacted therein at 160° C. for 72 hours with stirring at 250 rpm to obtain powder of pentacyl-type zeolite. This was washed five times with water, then dried at 120° C. for about 12 hours, and calcined. For calcination, the dried powder was first heated from room temperature up to 350° C., then further heated intermittently at one-hour intervals for 50° C. up in each interval finally up to 550° C., and kept at 550° C. for 3 hours. The calcined powder was shaped into tablets, which were then ground and dressed into grains having a grain size of from 0.7 to 1.4 mm.

Experiments for adsorption:

EXAMPLES 17 TO 24

Adsorbents 1 to 8 were tested for selective adsorption of chloropropylbenzene isomers to determine their selective adsorbability.

Precisely, 2.7 ml of a liquid-phase isomer mixture and 3.3 ml of the adsorbent that had been calcined at 500° C. were put into a 5 ml autoclave, and left therein at 130° C. for 30 minutes with intermittently stirring them. The liquid-phase mixture was comprised of n-nonane and chloropropylbenzene isomers (oI/mI/pI/oN/mN/pN=15/28/23/1/23/10) in a ratio of 5%/95%. To the mixture, n-nonane was added as the internal standard substance for gas chromatography, and this is substantially inert to the adsorbents in the adsorption experiments.

After having been contacted with the adsorbent, the liquid-phase mixture was analyzed through gas chromatography. From the data, the adsorption selectivity of the adsorbent to chloropropylbenzene isomers was obtained according to the formula defined above. The results are shown in Table 4, in which are also shown the most strongly-adsorbed component and the most weakly-adsorbed component.

TABLE 4

| | Example 17 Na—Y | Example 18 K—Y | Example 19 Rb—Y | Example 20 Cs—Y | Example 21 Mg—Y | Example 22 Ca—Y | Example 23 Sr—Y | Example 24 Ba—Y |
|---|---|---|---|---|---|---|---|---|
| (desorbent not used) | | | | | | | | |
| Adsorptivity (%) | 28 | 25 | 20 | 16 | 25 | 24 | 25 | 24 |
| αmN/oI | 1.34 | 1.62 | 1.76 | 1.12 | 1.54 | 1.62 | 1.34 | 1.60 |
| αmN/mI | 1.21 | 0.68 | 0.98 | 0.65 | 1.13 | 1.32 | 1.13 | 1.01 |
| αmN/pI | 1.57 | 0.34 | 1.01 | 1.29 | 1.62 | 2.04 | 1.30 | 0.52 |
| αmN/oN | 0.78 | 0.46 | 0.66 | 0.85 | 1.70 | 1.50 | 0.78 | 1.40 |
| αmN/pN | 1.25 | 1.26 | 0.88 | 0.99 | 1.17 | 1.36 | 1.09 | 0.85 |
| Most strongly-adsorbed component | oN | pI | oN | mI | mN | mN | oN | pI |
| Most weakly-adsorbed component | pI | oI | oI | pI | oN | pI | oI | oI |

Adsorptivity (%) is represented by (amount of adsorbed component, g)/(adsorbent, g).

EXAMPLES 25 TO 32

Adsorbents 11 to 18 were tested in the same manner as in Example 17. The resultants and also the most strongly-adsorbed component and the most weakly-adsorbed component are in Table 5.

TABLE 5

(desorbent not used)

|  | Example 25 Na—X | Example 26 K—X | Example 27 Rb—X | Example 28 Cs—X | Example 29 Mg—X | Example 30 Ca—X | Example 31 Sr—X | Example 32 Ba—X | Example 33 Na—MFI |
|---|---|---|---|---|---|---|---|---|---|
| Adsorptivity (%) | 18 | 17 | 16 | 16 | 16 | 16 | 16 | 16 | 10 |
| $\alpha mN/oI$ | 1.20 | 1.38 | 1.44 | 2.10 | 1.57 | 1.85 | 1.59 | 1.39 | 2.10 |
| $\alpha mN/mI$ | 0.89 | 0.84 | 0.72 | 0.71 | 1.12 | 1.24 | 1.37 | 0.74 | 1.50 |
| $\alpha mN/pI$ | 1.80 | 1.44 | 1.67 | 1.46 | 1.56 | 2.13 | 2.42 | 0.28 | 1.10 |
| $\alpha mN/oN$ | 1.10 | 0.86 | 1.20 | 1.80 | 1.02 | 0.60 | 0.56 | 1.47 | 0.52 |
| $\alpha mN/pN$ | 1.40 | 1.49 | 1.47 | 1.32 | 1.34 | 1.60 | 1.34 | 0.63 | 0.03 |
| Most strongly-adsorbed component | mN | mI | mI | mI | mN | oN | oN | pI | pN |
| Most weakly-adsorbed component | pI | pN | pI | oI | oI | pI | pI | oN | oI |

Adsorptivity (%) is represented by (amount of adsorbed component, g)/(adsorbent, g).

EXAMPLE 33

Adsorbent 25 was tested in the same manner as in Example 17, except that the liquid-phase mixture applied to the adsorbent was comprised of 1,3,5-triisopropylbenzene and chloropropylbenzene isomers (oI/mI/pI/oN/mN/pN=15/28/23/1/23/10) in a ratio of 5%/95%. The results and also the most storingly-adsorbed component and the most weakly-adsorbed component are in Table 5. 1,3,5-Triisopropylbenzene was added to the isomer mixture as the internal standard substance for gas chromatography, and this is substantially inert to the adsorbent in the adsorption experiments.

EXAMPLES 34 TO 40

Adsorbents 1, 2 and 4 to 8 were tested for selective adsorption of chloropropylbenzene isomers to determine their selective adsorbability.

Precisely, 2.7 ml of a liquid-phase isomer mixtures and 3.3 ml of the adsorbent that had been calcined at 500° C. were put into a 5 ml autoclave, and left therein at 130° C. for 30 minutes with intermittently stirring them. The liquid-phase mixture was comprised of o-chlorotoluene, n-nonane and chloropropylbenzene isomers (oI/mI/pI/oN/mN/pN=3/4/4/2/8/2) in a ratio of 70%/6%/24%. To the mixture, o-chlorotoluene was added as the desorbent, and n-nonane was added as the internal standard substance for gas chromatography, and these are both substantially inert to the adsorbents in the adsorption experiments.

After having been contacted with the adsorbent, the liquid-phase mixture was analyzed through gas chromatography. From the data, the adsorption selectivity of the adsorbent to chloropropylbenzene isomers was obtained according to the formula defined above. The results and also the most strongly-adsorbed component and the most weakly-adsorbed component are shown in Table 6.

TABLE 6

(desorbent: o-chlorotoluene)

|  | Example 34 Na—Y | Example 35 K—Y | Example 36 Cs—Y | Example 37 Mg—Y | Example 38 Ca—Y | Example 39 Sr—Y | Example 40 Ba—Y |
|---|---|---|---|---|---|---|---|
| Adsorptivity (%) | 29 | 25 | 20 | 26 | 25 | 24 | 24 |
| $\alpha mN/oI$ | 1.81 | 1.20 | 0.73 | 1.84 | 1.82 | 1.62 | 1.41 |
| $\alpha mN/mI$ | 1.30 | 0.55 | 0.58 | 1.11 | 1.21 | 1.15 | 0.76 |
| $\alpha mN/pI$ | 2.32 | 0.27 | 1.07 | 1.70 | 1.44 | 1.77 | 0.40 |
| $\alpha mN/oN$ | 1.09 | 0.75 | 0.91 | 1.23 | 1.10 | 1.07 | 1.28 |
| $\alpha mN/pN$ | 2.18 | 0.88 | 1.14 | 1.69 | 1.70 | 1.49 | 0.75 |
| Most strongly-adsorbed component | mN | pI | mI | mN | mN | mN | pI |
| Most weakly-adsorbed component | pI | oI | pN | oI | oI | pI | oI |

Adsorptivity (%) is represented by (amount of adsorbed component, g)/(adsorbent, g).

EXAMPLES 41 TO 48

Adsorbents 11, 12 and 14 to 19 were tested in the same manner as in Example 34. The results and also the most strongly-adsorbed component and the most weakly-adsorbed component are shown in Table 7.

raphy. From the data, the adsorption selectivity of the

TABLE 7

(desorbent: o-chlorotoluene)

|  | Example 41 Na—X | Example 42 K—X | Example 43 CS—X | Example 44 Mg—X | Example 45 Ca—X | Example 46 Sr—X | Example 47 Ba—X | Example 48 Ag—NaX |
|---|---|---|---|---|---|---|---|---|
| Adsorptivity (%) | 22 | 20 | 15 | 18 | 20 | 20 | 13 | 23 |
| αmN/oI | 2.46 | 1.13 | 1.87 | 1.66 | 1.41 | 2.11 | 1.25 | 2.11 |
| αmN/mI | 1.45 | 0.72 | 0.53 | 1.00 | 1.51 | 1.72 | 0.82 | 1.50 |
| αmN/pI | 4.24 | 1.37 | 1.39 | 1.92 | 2.42 | 2.58 | 0.66 | 2.90 |
| αmN/oN | 1.24 | 1.20 | 1.96 | 1.11 | 0.58 | 0.79 | 0.86 | 1.50 |
| amN/pN | 2.62 | 1.40 | 1.85 | 2.17 | 9.29 | 1.69 | 0.65 | 2.78 |
| Most strongly-adsorbed component | mN | mI | mI | mI | oN | oN | pN | mN |
| Most weakly-adsorbed component | pI | pN | oN | pN | pN | pI | oI | pI |

Adsorptivity (%) is represented by (amount of adsorbed component, g)/(adsorbent, g).

EXAMPLES 49 TO 55

Adsorbents 1, 2 and 4 to 8 were tested for selective adsorption of chloropropylbenzene isomers to determine their selective adsorbability.

Precisely, 2.7 ml of a liquid-phase isomer mixture and 3.3 ml of the adsorbent that had been calcined at 500° C. were put into a 5 ml autoclave, and left herein at 130° C. for 30 minutes with intermittently stirring them. The liquid-phase mixture was comprised of p-chlorotoluene, n-nonane and chloropropylbenzene isomers (oI/mI/pI/oN/mN/pN=3/5/4/2/8/2) in a ratio of 70%/5%/25%. To the mixture, p-chlorotoluene was added as the desorbent, and n-nonane was added as the internal standard substance for gas chromatography, and these are both substantially inert to the adsorbents in the adsorption experiments.

After having been contacted with the adsorbent, the liquid-phase mixture was analyzed through gas chromatography. From the data, the adsorption selectivity of the adsorbent to chloropropylbenzene isomers was obtained according to the formula defined above. The results and also the most strongly-adsorbed component and the most weakly-adsorbed component are shown in Table 8.

TABLE 8

(desorbent: p-chlorotoluene)

|  | Example 49 Na—Y | Example 50 K—Y | Example 51 Cs—Y | Example 52 Mg—Y | Example 53 Ca—Y | Example 54 Sr—Y | Example 55 Ba—Y |
|---|---|---|---|---|---|---|---|
| Adsorptivity (%) | 27 | 24 | 19 | 26 | 27 | 28 | 24 |
| αmN/oI | 1.43 | 0.99 | 1.23 | 1.71 | 2.04 | 1.37 | 1.09 |
| αmN/mI | 1.23 | 0.62 | 0.59 | 1.09 | 1.34 | 1.12 | 0.86 |
| αmN/pI | 2.61 | 0.39 | 2.51 | 1.98 | 2.12 | 1.84 | 0 91 |
| αmN/oN | 0.87 | 0.74 | 1.02 | 0.91 | 0.89 | 0.91 | 0392 |
| αmN/pN | 1.57 | 0.86 | 1.54 | 1.43 | 1.26 | 1.41 | 0.97 |
| Most strongly-adsorbed component | oN | pI | mI | oN | oN | oN | mI |
| Most weakly-adsorbed component | pI | mN | pI | pI | pI | pI | oI |

Adsorptivity (%) is represented by (amount of adsorbed component, g)/(adsorbent, g).

EXAMPLES 56 TO 63

Adsorbents 11, 12, and 14 to 19 were tested in the same manner as in Example 49. The results and also the most strongly-adsorbed component and the most weakly-adsorbed component are shown in Table 9.

TABLE 9

| | Example 56 Na—X | Example 57 K—X | Example 58 Cs—X | Example 59 Mg—X | Example 60 Ca—X | Example 61 Sr—X | Example 62 Ba—X | Example 63 Ag—NaX |
|---|---|---|---|---|---|---|---|---|
| | | | | (desorbent: p-chlorotoluene) | | | | |
| Adsorptivity (%) | 23 | 19 | 16 | 18 | 19 | 18 | 13 | 23 |
| αmN/oI | 1.51 | 1.14 | 2.13 | 1.71 | 2.02 | 1.90 | 1.15 | 1.33 |
| αmN/mI | 1.09 | 0.62 | 0.58 | 1.04 | 1.49 | 1.59 | 0.90 | 1.15 |
| αmN/pI | 3.52 | 2.03 | 2.59 | 2.02 | 2.66 | 2.21 | 0.72 | 3.66 |
| αmN/oN | 1.02 | 0.97 | 2.23 | 0.99 | 0.73 | 0.80 | 0.95 | 0.75 |
| αmN/pN | 2.22 | 1.61 | 2.21 | 1.24 | 1.36 | 1.71 | 0.89 | 3.64 |
| Most strongly-adsorbed component | mN | mI | mI | oN | oN | oN | pI | oN |
| Most weakly-adsorbed component | pI | pI | pI | pI | pI | pI | oI | pI |

Adsorptivity (%) is represented by (amount of adsorbed component, g)/(adsorbent, g).

EXAMPLES 64 TO 70

Adsorbents 1, 2 and 4 to 8 were tested for selective adsorption of chloropropylbenzene isomers to determine their selective adsorbability.

Precisely, 2.7 ml of a liquid-phase isomer mixture and 3.3 ml of the adsorbent that had been calcined at 500° C. were put into a 5 ml autoclave, and left therein at 130° C. for 30 minutes with intermittently stirring them. The liquid-phase mixture was comprised of chlorobenzene, n-nonane and chloropropylbenzene isomers (oI/mI/pI/oN/mN/pN=3/4/4/2/9/2) in a ratio of 71%/5%/24%. To the mixture chlorobenzene was added as the desorbent, and n-nonane was added as the internal standard substance for gas chromatography, and these are both substantially inert to the adsorbents in the adsorption experiments.

After having been contacted with the adsorbent, the liquid-phase mixture was analyzed through gas chromatography. From the data, the adsorption selectivity of the adsorbent to chloropropylbenzene isomers was obtained according to the formula defined above. The results and also the most strongly-adsorbed component and the most weakly-adsorbed component are shown in Table 10.

EXAMPLES 71 to 78

Adsorbents 11, 12, and 14 to 19 were tested in the same manner as in Example 64. The results and also the most strongly-adsorbed component and the most weakly-adsorbed component are shown in Table 11.

TABLE 10

| | Example 64 Na—Y | Example 65 K—Y | Example 66 Cs—Y | Example 67 Mg—Y | Example 68 Ca—Y | Example 69 Sr—Y | Example 70 Ba—Y |
|---|---|---|---|---|---|---|---|
| | | | (desorbent: chlorobenzene) | | | | |
| Adsorptivity (%) | 29 | 25 | 20 | 26 | 27 | 28 | 27 |
| αmN/oI | 1.27 | 0.78 | 0.64 | 1.56 | 1.72 | 1.49 | 1.11 |
| αmN/mI | 1.28 | 0.65 | 0.58 | 1.09 | 1.34 | 1.26 | 0.90 |
| αmN/pI | 2.88 | 0.34 | 1.62 | 1.70 | 1.84 | 2.10 | 0.52 |
| αmN/oN | 0.76 | 0.71 | 0.83 | 1.03 | 0.89 | 0.95 | 1.04 |
| αmN/pN | 1.50 | 1.11 | 1.29 | 1.44 | 1.59 | 1.47 | 0.86 |
| Most strongly-adsorbed component | oN | pI | mI | mN | oN | oN | pI |
| Most weakly-adsorbed component | pI | pN | pI | pI | pI | pI | oI |

Adsorptivity (%) is represented by (amount of adsorbed component, g)/(adsorbent, g).

TABLE 11

(desorbent: chlorobenzene)

|  | Example 71 Na—X | Example 72 K—X | Example 73 Cs—X | Example 74 Mg—X | Example 75 Ca—X | Example 76 Sr—X | Example 77 Ba—X | Example 78 Ag—NaX |
|---|---|---|---|---|---|---|---|---|
| Adsorptivity (%) | 23 | 20 | 17 | 18 | 20 | 21 | 14 | 25 |
| αmN/oI | 0.86 | 0.87 | 1.44 | 1.75 | 1.67 | 1.94 | 1.22 | 0.76 |
| αmN/mI | 0.99 | 0.80 | 0.61 | 1.12 | 1.47 | 1.85 | 1.06 | 0.96 |
| αmN/pI | 2.34 | 1.63 | 1.18 | 1.26 | 2.18 | 2.28 | 0.63 | 2.83 |
| αmN/oN | 0.65 | 0.75 | 1.76 | 0.82 | 0.53 | 0.71 | 1.11 | 0.51 |
| αmN/pN | 1.61 | 2.15 | 2.04 | 2.12 | 1.54 | 1.45 | 0.66 | 1.79 |
| Most strongly-adsorbed component | oN | oN | mI | oN | oN | oN | pI | oN |
| Most weakly-adsorbed component | pI | pN | pN | pN | pI | pI | oI | pI |

Adsorptivity (%) is represented by (amount of adsorbed component, g)/(adsorbent, g).

EXAMPLES 79 TO 86

Adsorbents 17, 14, 11, and 20 to 24 were tested for selective adsorption of chloropropylbenzene isomers to determine their selective adsorbability.

Precisely, 2.7 ml of a liquid-phase isomer mixture and 3.3 ml of the adsorbent that had been calcined at 500° C. were put into a 5 autoclave, and left therein at 130° C. for 30 minutes with intermittently stirring them. The liquid-phase mixture was comprised of o-chlorotoluene, n-nonane and chloropropylbenzene isomers (oI/mI/pI/oN/mN/pN=16/23/8/20/21/11) in a ratio of 47%/6%/47%. To the mixture, o-chlorotoluene was added as the desorbent, and n-nonane was added as the internal standard substance for gas chromatography, and these are both substantially inert to the adsorbents in the adsorption experiments.

After having been contacted with the adsorbent, the liquid-phase mixture was analyzed through gas chromatography. From the data, the adsorption selectivity of the adsorbent to chloropropylbenzene isomers was obtained according to the formula defined above. The results and also the most strongly-adsorbed component and the most weakly-adsorbed component are shown in Table 12.

EXAMPLE 87

Adsorbents 9 were tested for selective adsorption of chloropropylbenzene isomers to determine their selective adsorbability, in the same manner as in Example 78 except that m-xylene was used herein as the desorbent. The liquid-phase mixture herein tested was comprised of m-xylene, n-nonane and chloropropylbenzene isomers (oI/mI/pI/oN/mN/pN=12/20/17/8/27/15) in a ratio of 47%/6%/47%.

TABLE 13

(desorbent: m-xylene)

|  | Example 87 Pb-KY |
|---|---|
| Adsorptivity (%) | 20 |
| αmN/oI | 0.85 |
| αmN/mI | 0.52 |
| αmN/pI | 0.31 |
| αmN/oN | 0.40 |
| αmN/pN | 0.55 |
| Most strongly-adsorbed component | pI |

TABLE 12

(desorbent: o-chlorotoluene)

|  | Example 79 Sr—X | Example 80 Cs—X | Example 81 Na—X | Example 82 10% Cs | Example 83 10% Tl | Example 84 10% Ag | Example 85 10% Li | Example 86 20% Li |
|---|---|---|---|---|---|---|---|---|
| Adsorptivity (%) | 20 | 15 | 22 | 20 | 20 | 22 | 24 | 23 |
| αmN/oI | 2.13 | 1.89 | 1.54 | 1.77 | 1.88 | 1.60 | 1.85 | 2.14 |
| αmN/mI | 1.85 | 0.56 | 1.15 | 0.83 | 0.93 | 1.51 | 1.21 | 1.10 |
| αmN/pI | 2.93 | 1.45 | 2.36 | 2.80 | 2.93 | 4.33 | 2.91 | 2.95 |
| αmN/oN | 0.79 | 1.75 | 0.92 | 1.29 | 1.22 | 0.73 | 1.07 | 1.23 |
| αmN/pN | 1.59 | 2.29 | 1.86 | 2.85 | 2.14 | 4.58 | 2.30 | 2.69 |
| Most strongly-adsorbed component | oN | mI | oN | mI | mI | oN | mN | mN |
| Most weakly-adsorbed component | pI | pN | pI | pN | pI | pN | pI | pI |

Adsorptivity (%) is represented by (amount of adsorbed component, g)/(adsorbent, g).

TABLE 13-continued (desorbent: m-xylene)

|  | Example 87 Pb-KY |
| --- | --- |
| Most weakly-adsorbed component | mN |

Adsorptivity (%) is represented by (amount of adsorbed component, g)/(adsorbent, g).

EXAMPLES 88 AND 89

Adsorbents 9 and 10 were tested for selective adsorption of chloropropylbenzene isomers to determine their selective adsorbability, in the same manner as in Example 87 except that o-xylene was used herein as the desorbent. The liquid-phase mixture herein tested was comprised of o-xylene, n-nonane and chloropropylbenzene isomers (oI/mI/pI/oN/mN/pN=12/20/17/8/27/15) in a ratio of 47%/6%/47%.

TABLE 14

(desorbent: o-xylene)

|  | Example 88 Pb-KY | Example 39 Cs-Pb-KY |
| --- | --- | --- |
| Adsorptivity (%) | 21 | 17 |
| αmN/oI | 0.71 | 0.63 |
| αmN/mI | 0.58 | 0.49 |
| αmN/pI | 0.38 | 0.32 |
| αmN/oN | 0.40 | 0.31 |
| αmN/pN | 0.84 | 0.77 |
| Most strongly-adsorbed component | pI | oN |
| Most weakly-adsorbed component | mN | mN |

Adsorptivity (%) is represented by (amount of adsorbed component, g)/(adsorbent, g).

While the invention has been described in detail and with reference to specific embodiments thereof, it will be apparent to one skilled in the art that various changes and modifications can be made therein without departing from the spirit and scope thereof.

What is claimed is:

1. A method for producing aromatic compounds having an alkyl group comprising at least 3 carbon atoms, which comprises steps (1) and (2):

(1) a step of contacting a feed that contains an aromatic compound bonded to a branched alkyl group having at least 3 carbon atoms, with a zeolite-containing catalyst in a liquid phase in the presence of hydrogen therein, thereby changing the relative positions of the carbon atoms of said alkyl group bonded to the aromatic ring of the compound; and (2) a step of treating a mixture of isomers of an aromatic compound bonded to an alkyl group having at least 3 carbon atoms, with a zeolite adsorbent that contains at least one exchangeable cation selected from the group consisting of alkali metals, alkaline earth metals, lead, thallium and silver, and separating the isomerized compound from the isomer mixture through adsorption, wherein the step (1) of changing the relative positions of the carbon atoms of the alkyl group that is bonded to the aromatic ring of the starting compound are/is for at least one type of conversion of the following (a) to (c):

(a) conversion reducing the number of branches of said alkyl group, (b) conversion shortening branched side chains of said alkyl group, (c) conversion changing the alkyl group into a different alkyl group having a secondary carbon that bonds to the aromatic ring via said secondary carbon.

2. The method as claimed in claim 1, wherein the starting material in the step (1) contains an additional aromatic compound that differs from the aromatic compound having an alkyl group to be processed therein.

3. The method claimed in claim 1, wherein said aromatic compound is processed in said step (2) and additionally comprises at least one halogen substituent.

4. The method claimed in claim 1, wherein isomers of said aromatic compound having an alkyl group, wherein the number of the branches of said alkyl group differs from each other, are separated in said step (2).

5. The method claimed in claim 1, wherein a fajuasite-type zeolite is the zeolite used in said step (2).

6. The method claimed in claim 1, wherein, in said step (2), an m-halogenated n-alkylbenzene or an m-halogenated sec-alkylbenzene is separated through adsorption from a mixture of isomers of a halogenated alkylbenzene of the following formula:

(formula 1)

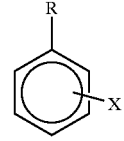

wherein R represents an alkyl group having at least 3 carbon atoms, and X represents a halogen atom.

7. The method claimed in claim 1, wherein at least one desorbent selected from the group consisting of chlorotoluene isomers, xylene isomers and chlorobenzene is desorbent used in step (2).

8. A method for producing aromatic compound derivatives having an alkyl group having at least 3 carbon atoms, which compares oxidizing or halogenating the alkyl group of the aromatic compounds as produced in claim 1.

9. A process for conversion of isoalkylbenzene to n-alkylbenzene, wherein alkyl means propyl or butyl, with our without halogenation, comprising reacting said isoalkylbenzene with an acid-type zeolite in a liquid medium in the presence of hydrogen therein, thereby rearranging isoalkyl carbon atoms into the n-alkyl carbon atom configuration.

10. The method as claimed in claim 1, wherein the zeolite containing catalyst contains rhenium and/or silver.

* * * * *

UNITED STATES PATENT AND TRADEMARK OFFICE
CERTIFICATE OF CORRECTION

PATENT NO.    : 6,462,248 B1
DATED         : October 8, 2002
INVENTOR(S)   : Nakatani et al.

It is certified that error appears in the above-identified patent and that said Letters Patent is hereby corrected as shown below:

Column 10,
Line 10, please insert the following paragraph:

-- The method for the treatment is not specifically defined. For example, it is preferable that the catalyst is dispersed in an aqueous solution containing at least one selected from hydrochloric acid, ethylenediamine-tetraacetic acid and tartaric acid, and stirred therein. The temperature for the treatment preferable falls between room temperature and 100°C. --
Line 20, please delete the entire paragraph beginning with "In the method".

Column 38,
Table 8, at the subheading "Example 55" at "αmN/oN" please change "0392" to
-- 0.92 --.

Signed and Sealed this

Second Day of December, 2003

JAMES E. ROGAN
*Director of the United States Patent and Trademark Office*